US009410189B2

(12) United States Patent
Satterfield

(10) Patent No.: US 9,410,189 B2
(45) Date of Patent: Aug. 9, 2016

(54) METHODS OF PREVENTING NON-SPECIFIC REACTIONS OF NUCLEOTIDE SEQUENCES

(75) Inventor: Brent C Satterfield, Greenwood, SC (US)

(73) Assignee: Co-Diagnostics, Inc., Sandy, UT (US)

( * ) Notice: Subject to any disclaimer, the term of this patent is extended or adjusted under 35 U.S.C. 154(b) by 549 days.

(21) Appl. No.: 13/098,348

(22) Filed: Apr. 29, 2011

(65) Prior Publication Data

US 2012/0045796 A1 Feb. 23, 2012

Related U.S. Application Data

(60) Provisional application No. 61/330,282, filed on Apr. 30, 2010.

(51) Int. Cl.
| | | |
|---|---|---|
| *C12Q 1/68* | (2006.01) | |
| *C12N 15/10* | (2006.01) | |
| *C12Q 1/70* | (2006.01) | |
| *C07H 21/04* | (2006.01) | |

(52) U.S. Cl.
CPC .......... *C12Q 1/6844* (2013.01); *C12N 15/1096* (2013.01); *C12Q 1/689* (2013.01); *C12Q 1/6848* (2013.01); *C12Q 1/701* (2013.01)

(58) Field of Classification Search
USPC ........................................................ 435/91.2
See application file for complete search history.

(56) References Cited

U.S. PATENT DOCUMENTS

| | | | | |
|---|---|---|---|---|
| 5,688,642 | A * | 11/1997 | Chrisey et al. ................ 435/6.11 |
| 6,830,902 | B1 * | 12/2004 | Astatke ................ C12Q 1/6844 |
| | | | | 435/7.1 |
| 7,354,719 | B2 * | 4/2008 | Norman et al. ............... 435/6.14 |
| 8,530,194 | B2 * | 9/2013 | Mao ..................... C12Q 1/6848 |
| | | | | 435/7.1 |
| 2009/0130720 | A1 * | 5/2009 | Nelson et al. ................. 435/91.2 |

FOREIGN PATENT DOCUMENTS

| | | | | |
|---|---|---|---|---|
| WO | WO2006122409 | * | 11/2006 | ......... A61K 31/7088 |
| WO | WO2006130949 | * | 12/2006 | ......... A61K 31/7088 |
| WO | WO2007022642 | * | 3/2007 | ......... A61K 31/7088 |
| WO | WO2007038422 | * | 4/2007 | ............... C12Q 1/68 |
| WO | WO2010056499 | * | 5/2010 | ............... C12Q 1/68 |
| WO | WO2010075414 | * | 7/2010 | |

OTHER PUBLICATIONS

Dolinnaya NG, Borisova OA. [Sulfur-containing nucleic acids. Synthesis, chemical behavior in supramolecular biopolymer complexes, biological properties]. Mol Biol (Mosk). Nov.-Dec. 2000;34(6):931-45. Review. Russian.*
Hatta T, Kim SG, Nakashima H, Yamamoto N, Sakamoto K, Yokoyama S, Takaku H. Mechanisms of the inhibition of reverse transcription by unmodified and modified antisense oligonucleotides. FEBS Lett. Sep. 13, 1993;330(2):161-4.*
Hatta T, Takai K, Yokoyama S, Nakashima H, Yamamoto N, Takaku H. Phosphorothioate oligonucleotides block reverse transcription by the Rnase H activity associated with the HIV-1 polymerase. Biochem Biophys Res Commun. Jun. 26, 1995;211(3):1041-6.*
Gao WY, Stein CA, Cohen JS, Dutschman GE, Cheng YC. Effect of phosphorothioate homo-oligodeoxynucleotides on herpes simplex virus type 2-induced DNA polymerase. J Biol Chem. Jul. 5, 1989;264(19):11521-6.*
Xodo L, Alunni-Fabbroni M, Manzini G, Quadrifoglio F. Pyrimidine phosphorothioate oligonucleotides form triple-stranded helices and promote transcription inhibition. Nucleic Acids Res. Aug. 25, 1994;22(16):3322-30.*
Alunni-Fabbroni M, Manfioletti G, Manzini G, Xodo LE. Inhibition of T7 RNA polymerase transcription by phosphate and phosphorothioate triplex-forming oligonucleotides targeted to a R.Y site downstream from the promoter. Eur J Biochem. Dec. 15, 1994;226(3):831-9.*
Guga P, Kozionciewicz M. Phosphorothioate nucleotides and oligonucleotides—recent progress in synthesis and application. Chem Biodivers. Sep. 2011;8(9):1642-81. Review.*
Ghosh MK, Ghosh K, Dahl O, Cohen JS. Evaluation of some properties of a phosphorodithioate oligodeoxyribonucleotide for antisense application. Nucleic Acids Res. Dec. 11, 1993;21(24):5761-6.*
Ott J, Eckstein F. Protection of oligonucleotide primers against degradation by DNA polymerase I. Biochemistry. Dec. 15, 1987;26(25):8237-41.*
Suggs JW, Taylor DA. Use of phosphorothioate analogs of poly(dA-dT).poly(dAdT) to study steroidal-diamine induced conformational change in poly(dA-dT).poly(dA-dT). FEBS Lett. Sep. 9, 1985;189(1):77-80.*
Marshall WS, Beaton G, Stein CA, Matsukura M, Caruthers MH. Inhibition of human immunodeficiency virus activity by phosphorodithioate oligodeoxycytidine. Proc Natl Acad Sci U S A. Jul. 15, 1992;89(14):6265-9.*
Kutyavin IV, Rhinehart RL, Lukhtanov EA, Gorn VV, Meyer RB Jr, Gamper HB Jr. Oligonucleotides containing 2-aminoadenine and 2-thiothymine act as selectively binding complementary agents. Biochemistry. Aug. 27, 1996;35(34):11170-6.*
Romaniuk PJ, Eckstein F. A study of the mechanism of T4 DNA polymerase with diastereomeric phosphorothioate analogues of deoxyadenosine triphosphate. J Biol Chem. Jul. 10, 1982;257(13):7684-8.*
Bellon L, Barascut JL, Maury G, Divita G, Goody R, Imbach JL. 4'-Thio-oligo-beta-D-ribonucleotides: synthesis of beta-4"-thio-oligouridylates, nuclease resistance, base pairing properties, and interaction with HIV-1 reverse transcriptase. Nucleic Acids Res. Apr. 11, 1993;21(7):1587-93.*
Eckstein F. Phosphorothioate oligodeoxynucleotides: what is their origin and what is unique about them? Antisense Nucleic Acid Drug Dev. Apr. 2000;10(2):117-21. Review.*
Burgers PM, Eckstein F. A study of the mechanism of DNA polymerase I from *Escherichia coli* with diastereomeric phosphorothioate analogs of deoxyadenosin triphosphate. J Biol Chem. Aug. 10, 1979;254(15):6889-93.*
Eckstein F. Nucleoside phosphorothioates. Annu Rev Biochem. 1985;54:367-402. Review.*

(Continued)

*Primary Examiner* — Samuel Woolwine
*Assistant Examiner* — Olayinka Oyeyemi
(74) *Attorney, Agent, or Firm* — Meunier Carlin & Curfman LLC

(57) ABSTRACT

Disclosed herein are methods of nucleic acid amplification, including methods of preventing non-specific reaction of a nucleotide sequence with a DNA modifying enzyme.

5 Claims, 7 Drawing Sheets

(56) References Cited

OTHER PUBLICATIONS

Skerra A. Phosphorothioate primers improve the amplification of DNA sequences by DNA polymerases with proofreading activity. Nucleic Acids Res. Jul. 25, 1992;20(14):3551-4.*

Bjergårde K, Dahl O. Solid phase synthesis of oligodeoxyribonucleoside phosphorodithioates from thiophosphoramidites. Nucleic Acids Res. Nov. 11, 1991; 19(21):5843-50.*

Kainz P, Schmiedlechner A, Strack HB. Specificity-enhanced hot-start PCR: addition of double-stranded DNA fragments adapted to the annealing temperature. Biotechniques. Feb. 2000; 28(2):278-82.*

Maury G, el Alaoui A, Morvan F, Müller B, Imbach JL, Goody RS. Template. Phosphorothioate oligonucleotides duplexes as inhibitors of HIV-1 reverse transcriptase. Biochem Biophys Res Commun. Aug. 14, 1992; 186(3):1249-56.*

Oguro M, Nagano H. Inhibition of eukaryotic DNA polymerase-alpha by polydeoxynucleotides. J Biochem. Aug. 1982;92(2):599-602.*

Shimada T, Yamada M, Miwa M, Nagano H, Mano Y. Differential susceptibilities of DNA polymerases-alpha and -beta to polyanions. Nucleic Acids Res. Sep. 1978; 5(9):3427-38.*

Stein CA, Cheng YC. Antisense oligonucleotides as therapeutic agents—is the bullet really magical? Science. Aug. 20, 1993; 261(5124):1004-12.*

Yang X, Bassett SE, Li X, Luxon BA, Herzog NK, Shope RE, Aronson J, Prow TW, Leary JF, Kirby R, Ellington AD, Gorenstein DG. Construction and selection of bead-bound combinatorial oligonucleoside phosphorothioate and phosphorodithioate aptamer libraries designed for rapid PCR-based sequencing. Nucleic Acids Res.Dec. 1, 2002; 30(23):e132.*

* cited by examiner

SEQUENCE LISTING

<160> NUMBER OF SEQ ID NOS: 38

<210> SEQ ID NO 1
<211> LENGTH: 30
<212> TYPE: DNA
<213> ORGANISM: Artificial Sequence
<220> FEATURE:
<223> OTHER INFORMATION: synthethic oligonucleotide

<400> SEQUENCE: 1
ggaagctgta cgcgactagt ggttagagga                                         30

<210> SEQ ID NO 2
<211> LENGTH: 23
<212> TYPE: DNA
<213> ORGANISM: Dengue virus

<400> SEQUENCE: 2
ctgtgcctgg agagacagca gga                                                23

<210> SEQ ID NO 3
<211> LENGTH: 35
<212> TYPE: DNA
<213> ORGANISM: Artificial Sequence
<220> FEATURE:
<223> OTHER INFORMATION: synthethic oligonucleotide

<400> SEQUENCE: 3
acagcatatt gacgctggga aagaccagag cgtca                                   35

<210> SEQ ID NO 4
<211> LENGTH: 19
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 4
aaaaaaaaaa aaaaaaaaa                                                     19

<210> SEQ ID NO 5
<211> LENGTH: 19
<212> TYPE: DNA
<213> ORGANISM: Treponema pallidum

<400> SEQUENCE: 5
gcggtgaggg gaatgtcta                                                     19

<210> SEQ ID NO 6
<211> LENGTH: 26
<212> TYPE: DNA
<213> ORGANISM: Treponema pallidum

<400> SEQUENCE: 6
cagcaaacgt tgacttaaaa tcagga                                             26

<210> SEQ ID NO 7
<211> LENGTH: 40
<212> TYPE: DNA
<213> ORGANISM: Artificial Sequence
<220> FEATURE:
<223> OTHER INFORMATION: synthethic oligonucleotide

<400> SEQUENCE: 7
agaggcaacc ctgcactgtt atggggccta cctggttgcc         40

<210> SEQ ID NO 8
<211> LENGTH: 19
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 8
taccgccgcc gctcgttca         19

<210> SEQ ID NO 9
<211> LENGTH: 20
<212> TYPE: DNA
<213> ORGANISM: XMLV

<400> SEQUENCE: 9
actgtggcaa atggggatgt         20

<210> SEQ ID NO 10
<211> LENGTH: 22
<212> TYPE: DNA
<213> ORGANISM: XMLV

<400> SEQUENCE: 10
tggagaccga ggaatcataa ca         22

<210> SEQ ID NO 11
<211> LENGTH: 49
<212> TYPE: DNA
<213> ORGANISM: Artificial Sequence
<220> FEATURE:
<223> OTHER INFORMATION: synthethic oligonucleotide

<400> SEQUENCE: 11
atcatgggac ctaatttccc ttaagcgagg aaacactcct aggtcccat         49

<210> SEQ ID NO 12
<211> LENGTH: 189
<212> TYPE: DNA
<213> ORGANISM: XMLV

<400> SEQUENCE: 12
tactgtggca aatggggatg tgagaccact ggacaggcat actggaagcc atcatcatca         60
tgggacctaa tttcccttaa gcgaggaaac actcctaagg atcagggccc ctgttatgat        120
tcctcggtct ccagtggcgt ccagggtgcc acaccggggg gtcgatgcaa ccccctggtc        180
ttagaattc        189

<210> SEQ ID NO 13
<211> LENGTH: 17
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 13
aaaaaaaaaa aaaaaaa         17

<210> SEQ ID NO 14
<211> LENGTH: 21

```
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 14
aaaaaaaaaa aaaaaaaaaa a                                              21

<210> SEQ ID NO 15
<211> LENGTH: 23
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 15
aaaaaaaaaa aaaaaaaaaa aaa                                            23

<210> SEQ ID NO 16
<211> LENGTH: 25
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 16
aaaaaaaaaa aaaaaaaaaa aaaaa                                          25

<210> SEQ ID NO 17
<211> LENGTH: 200
<212> TYPE: DNA
<213> ORGANISM: Treponema pallidum

<400> SEQUENCE: 17
gttccccatt gtggcaaaga aggatttcaa gtaccgcggt gaggggaatg tctatcacga    60
agggttctgc aaagacgata gaggcaaccc tgcactgtta tggggcctac ctgaccattg   120
ggaagaatcc tgattttaag tcaacgtttg ctgttttgtg ggagtctaag ggagataagc   180
cggtgtatga gccggggttt                                               200

<210> SEQ ID NO 18
<211> LENGTH: 34
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 18
aaaaaaaaaa aaaaaaaaaa aaaaaaaaaa aaaa                                34

<210> SEQ ID NO 19
<211> LENGTH: 38
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 19
aaaaaaaaaa aaaaaaaaaa aaaaaaaaaa aaaaaaaa                            38
```

```
<210> SEQ ID NO 20
<211> LENGTH: 42
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 20
aaaaaaaaaa aaaaaaaaaa aaaaaaaaaa aaaaaaaaaa aa                              42

<210> SEQ ID NO 21
<211> LENGTH: 46
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 21
aaaaaaaaaa aaaaaaaaaa aaaaaaaaaa aaaaaaaaaa aaaaaa                          46

<210> SEQ ID NO 22
<211> LENGTH: 34
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 22
atatatatat atatatatat atatatatat atat                                       34

<210> SEQ ID NO 23
<211> LENGTH: 38
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 23
atatatatat atatatatat atatatatat atatatat                                   38

<210> SEQ ID NO 24
<211> LENGTH: 42
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 24
atatatatat atatatatat atatatatat atatatatat at                              42

<210> SEQ ID NO 25
<211> LENGTH: 46
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 25
atatatatat atatatatat atatatatat atatatatat atatat                          46

<210> SEQ ID NO 26
```

```
<211> LENGTH: 50
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 26
atatatatat atatatatat atatatatat atatatatat atatatatat                 50

<210> SEQ ID NO 27
<211> LENGTH: 68
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 27
actgactgac tgactgactg actgactgac tgactgactg actgactgac tgactgactg      60
actgactg                                                               68

<210> SEQ ID NO 28
<211> LENGTH: 76
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 28
actgactgac tgactgactg actgactgac tgactgactg actgactgac tgactgactg      60
actgactgat cgatcg                                                      76

<210> SEQ ID NO 29
<211> LENGTH: 84
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 29
actgactgac tgactgactg actgactgac tgactgactg actgactgac tgactgactg      60
actgactgac tgactgactg actg                                             84

<210> SEQ ID NO 30
<211> LENGTH: 92
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 30
actgactgac tgactgactg actgactgac tgactgactg actgactgac tgactgactg      60
actgactgac tgactgactg actgactgac tg                                    92

<210> SEQ ID NO 31
<211> LENGTH: 100
<212> TYPE: DNA
<213> ORGANISM: Artificial Sequence
<220> FEATURE:
<223> OTHER INFORMATION: synthethic oligonucleotide with modified base
      having phosphorthioate linkage
```

```
<400> SEQUENCE: 31
actgactgac tgactgactg actgactgac tgactgactg actgactgac tgactgactg    60
actgactgac tgactgactg actgactgac tgactgactg                         100

<210> SEQ ID NO 32
<211> LENGTH: 32
<212> TYPE: DNA
<213> ORGANISM: Dengue virus
<220> FEATURE:
<223> OTHER INFORMATION: synthethic oligonucleotide with modified base
      having phosphorthioate linkage

<400> SEQUENCE: 32
ggaagctgta cgcgactagt ggttagagga ga                                  32

<210> SEQ ID NO 33
<211> LENGTH: 179
<212> TYPE: DNA
<213> ORGANISM: Artificial Sequence
<220> FEATURE:
<223> OTHER INFORMATION: synthethic oligonucleotide

<400> SEQUENCE: 33
ggaagctgta cgcgtggcat attggactag cggttagagg agacccctcc caccactgac    60
aaaacgcagc aaaaggggc ccgaagccag gaggaagctg tactcctggt ggaaggacta   120
gaggttagag gagaccccc caacacaaaa acagcatatt gacgctggga aagaccaga    179

<210> SEQ ID NO 34
<211> LENGTH: 179
<212> TYPE: DNA
<213> ORGANISM: Dengue virus

<400> SEQUENCE: 34
ggaagctgta cgcgtggcat attggactag cggttagagg agacccctcc caccactgac    60
aaaacgcagc aaaaggggc ccgaagccag gaggaagctg tactcctggt ggaaggacta   120
gaggttagag gagaccccc caacacaaaa acagcatatt gacgctggga aagaccaga    179

<210> SEQ ID NO 35
<211> LENGTH: 24
<212> TYPE: DNA
<213> ORGANISM: Hepatitis B virus

<400> SEQUENCE: 35
aggaggctgt aggcataaat tggt                                           24

<210> SEQ ID NO 36
<211> LENGTH: 20
<212> TYPE: DNA
<213> ORGANISM: Hepatitis B virus

<400> SEQUENCE: 36
acagcttgga ggcttgaaca                                                20

<210> SEQ ID NO 37
<211> LENGTH: 42
<212> TYPE: DNA
<213> ORGANISM: Artificial Sequence
<220> FEATURE:
<223> OTHER INFORMATION: synthethic oligonucleotide

<400> SEQUENCE: 37
```

```
caccagcacc atgcaacttt ttcacctctg cctacatggt gc                              42

<210> SEQ ID NO 38
<211> LENGTH: 30
<212> TYPE: DNA
<213> ORGANISM: Artificial Sequence
<220> FEATURE:
<223> OTHER INFORMATION: synthethic oligonucleotide with modified base
      having phosphorthioate linkage

<400> SEQUENCE: 38
ccgatacgcg atgcgactgt gcagcatgca                                            30
```

METHODS OF PREVENTING NON-SPECIFIC REACTIONS OF NUCLEOTIDE SEQUENCES

CROSS-REFERENCE TO RELATED APPLICATIONS

This application claims priority to U.S. Provisional Application No. 61/330,282, filed on Apr. 30, 2010 and entitled NUCLEIC ACID HOTSTART TECHNOLOGY, which is incorporated herein by reference in its entirety.

REFERENCE TO SEQUENCE LISTING

The Sequence Listing in electronic format. The Sequence Listing is provided as a file entitled CDIAG011A.TXT, created Nov. 2, 2011, which is 9.00 KB in size. The information in the electronic format of the Sequence Listing is incorporated herein by reference in its entirety.

BACKGROUND

1. Field

The present technology pertains to the field of "hot starts" for enzymes that act upon nucleic acids, such as for example, polymerases.

2. Description of the Related Art

The invention of the polymerase chain reaction (PCR) has made DNA diagnostics and forensics possible. Saiki et al., "Enzymatic amplification of beta-globin genomic sequences and restriction site analysis for diagnosis of sickle cell anemia." *Science,* 230, 1350-1354 (1985).(1) By adding the reverse transcriptase present in retroviruses to the reaction, the utility of PCR was expanded to RNA.

A common problem with PCR is non-specific amplification of nucleic acids during PCR set-up and before the initial denaturation and amplification steps. The non-specific activity of the enzymes, for example, at room temperature can result in unwanted background products and the formation of primer-dimers. These unwanted products can interfere with generating the desired amplicons and can provide false signals when using PCR as a diagnostic tool. Many enzymes that act upon DNA, including DNA polymerases and reverse transcriptases can suffer from problems with non-specific activity.

Low specificity during PCR set up for the polymerase has been overcome through the use of various "hot start" methods. Such methods include, the use of temperature controlled magnesium concentration, and the use of temperature activated dNTP's and primers. The most commonly available reagents commercially utilize chemically modified or antibody inhibited polymerases.

Reverse transcriptase (RT) is capable of adding bases to the 3' ends of the primers during room temperature PCR setup even in the absence of RNA.(2) The extra bases added to the primers can inhibit amplification of the intended target, leading to false negatives and/or causing primer-dimers. While some of the above-described methods could conceivably be adapted for temperature dependent activation of the reverse transcriptase, most require temperatures that would denature the RT and consequently are not viable for use with RT.

While various PCR "hot start" technologies exist, embodiments described herein provide new approaches, including approaches that can be used with RT PCR, as well as other enzymes that act upon nucleic acid molecules.

SUMMARY

Embodiments herein generally relate to methods and materials used to inhibit enzyme activity. For example, some embodiments relate to "hotstart" methods that can be used with a variety of enzymes, which enzymes act upon or modify nucleic acids. In particular, the methods and materials can be used with polymerases and reverse transcriptases.

Some embodiments herein relate temperature dependent inhibition of a polymerase or other nucleic acid modifying molecule to inhibit the polymerase at lower temperatures, thereby reducing nonspecific interactions while maintaining the activity of the enzyme at elevated temperatures where specificity is enhanced.

Some embodiments relate to the surprising and unexpected discover that when oligonucleotides can be used to inhibit enzymes at certain temperatures. For example, oligonucleotides modified to include sulfur atoms can be used. One non-limiting example of such oligonucleotides are those with phosphorothioate backbones (S-oligos). It is believed that the sulfur molecule in the linkage creates a "sticky" bond. This means that the polymerase or other enzyme is less likely to release an S-oligo than a normal nucleic acid. Since the S-oligo becomes stuck in the nucleic acid binding site (or stuck in another location that inhibits the enzyme), it reduces the activity of the enzyme. However, by increasing the temperature, an S-oligo as described herein can be released, allowing enzymatic activity to resume at the desired temperature.

The temperature dependent nature of oligonucleotides such as s-oligos has not been previously demonstrated, nor has the temperature dependent inhibition and its consequent utility in providing "hotstart" technologies for a variety of polymerases has not previously been demonstrated. The present technology reveals this temperature dependent mechanism of inhibition and illustrates the utility in creating "hotstart" technologies for a variety of polymerases, including, but not limited to DNA polymerases and Reverse Transcriptases.

Some embodiments relate to methods of preventing non-specific reaction of a nucleotide sequence with a DNA modifying enzyme. The methods can include, for example, providing an oligonucleotide that includes, for example, from about 5 to about 50 nucleotides, wherein about 40% to 100% of the nucleotides include a sulfur atom; and contacting the oligonucleotide with at least one nucleic acid modifying enzyme.

In some embodiments the sulfur atom may be part of a phosphorothioate linkage, for example. The phosphorothioate linkage can include, for example, at least 50%, at least 70%, at least 90%, or more of the oligonucleotide.

The nucleic acid modifying enzyme can be, for example, one or more of a polymerase, a reverse transcriptase or other nucleic acid modifying enzyme. The polymerase can be for example, any polymerase, including those listed herein and known to those of skill in the art. Non-limiting examples of polymerases include DNA or RNA polymerases from eukaryotic or prokaryotic organisms. DNA polymerases from any of families A (e.g., T7 DNA polymerase, mitochondrial DNA polymerase γ, DNA pol 1, *Thermus aquaticus pol* 1, and *Bacillus stearothermophilus* pol 1), B (e.g., DNA polymerases α, δ, ε; DNA polymerase ζ; T4 polymerase; Phi29 polymerase; RB69 polymerase), C (e.g., DNA Polymerase III alpha subunit; DNA Polymerase III epsilon subunit), D (e.g., polymerases from Euryarchaeota subdomain of Archaea), X (e.g., pol β, pol σ, pol λ, pol μ, terminal deoxynucleotidyl transferase (TdT), Pol X polymerase from *Saccharomyces cerevisiae*—pol4), Y (e.g., translesion synthesis (TLS) polymerases; Pol η (eta), Polζ (zeta) (polymerase ζ is a B Family polymerase a complex of the catalytic subunit REV3L with Rev7, which associates with Rev1), Pol ι (iota), Pol κ (kappa), and Rev1 (terminal deoxycytidyl transferase), *E. coli*, Pol IV (DINB) and PolV (UmuD'$_2$C)), or RT (e.g, RNA-dependent DNA polymerase, telomerase, HIV-1 reverse transcriptase, M-MLV reverse transcriptase, AMV reverse transcriptase). In some aspects the polymerase may be, for example, a DNA polymerase such as for example DNA polymerase, DNA polymerasae I-V, Taq Polymerase, Tfl (*Thermus flavus*) DNA polymerase, Tth (*Thermus thermophilus*) DNA polymerase, and Pfu (*Pyrococcus furiosus*) DNA polymerase. In some aspects, the reverse transcriptase can be, for example, reverse transcriptase, ImProm-II™ Reverse Transcriptase, GoScript™ Reverse Transcriptase, AMV Reverse Transcriptase, or M-MLV Reverse Transcriptase.

In some embodiments the oligonucleotide can include, for example, between 10 and 30 polyA bases, polyAT bases or polyACTG bases. In some embodiments the oligonucleotide can have or include, for example a sequence of any of the SEQ ID NOs disclosed herein.

In some aspects, the oligonucleotide may be at least part of a PCR primer or probe. In some aspects, the oligonucleotide preferably is not complementary to more than 1 to about 15 bases of an amplification product, preferably not to more than 2-10 bases of the amplification product, or more preferably not complementary to more than 1 base of an amplification product. In some aspects the oligonucleotide is not the PCR primer or probe.

Some embodiments relate to methods of preventing non-specific reaction of a nucleotide sequence with a DNA modifying enzyme. The methods can include, for example, providing an oligonucleotide that includes from about 5 to about 50 nucleotides, wherein the nucleotides include one or more sulfur atoms in an amount sufficient to stick or interfere at room temperature or a desired temperature, but release when heated to a desired temperature.

Some embodiments relate to method of nucleic acid amplification, which can include, for example, providing an oligonucleotide that includes from about 5 to about 50 nucleotides, wherein about 40% to 100% of the nucleotides include a sulfur atom and contacting the oligonucleotide with a polymerase. In some embodiments the nucleic acid amplification may be RT PCR and the polymerase may be reverse transcriptase, for example. The methods further may include, for example a DNA polymerase.

Some embodiments relate to kits that include a sulfur-containing oligonucleotide and one or more of a nucleic acid modifying enzyme; a PCR primer specific for a target nucleic acid sequence; a probe, a plurality of dNTPs; and a control sample. The sulfur-containing oligonucleotide may include, for example, a phosphorothioate linkage and/or a phosphorodithioate linkage. In some aspects the oligonucleotide may have, for example, at least 50% to 100% phosphorothioate linkages and/or phosphorodithioate linkages. The kits can include, for example, a plurality of dNTPs. The kits may be, for example, PCR diagnostic kits, including, for example, one or more of Roche diagnostic tests COBAS HIV-1, COBAS HBV, COBAS HCV, COBAS CMV, Amplicor HIV-1, Amplicor HCV, Amplicor HBV, Amplicor HPV, Amplicor CT/NG, COBAS MPX, COBAS WNV, or Novartis tests Procleix WNV, Procleix HIV/HCV or Procleix Ultrio.

The nucleic acid modifying enzyme of the kits may be, for example, one or more of a polymerase, a reverse transcriptase, or the like. The polymerase can be for example, any polymerase, including those listed herein and known to those of skill in the art. Non-limiting examples of polymerases include DNA or RNA polymerases from eukaryotic or prokaryotic organisms. DNA polymerases from any of families A (e.g., T7 DNA polymerase, mitochondrial DNA polymerase γ, DNA pol 1, *Thermus aquaticus* pol 1, and *Bacillus stearothermophilus* pol 1), B (e.g., DNA polymerases α, δ, ε; DNA polymerase ζ; T4 polymerase; Phi29 polymerase; RB69 polymerase), C (e.g., DNA Polymerase III alpha subunit; DNA Polymerase III epsilon subunit), D (e.g., polymerases from Euryarchaeota subdomain of Archaea), X (e.g., pol β, pol σ, pol λ, pol µ, terminal deoxynucleotidyl transferase (TdT), Pol X polymerase from *Saccharomyces cerevisiae*—pol4), Y (e.g., translesion synthesis (TLS) polymerases; Pol η (eta), Polζ (zeta) (polymerase ζ is a B Family polymerase a complex of the catalytic subunit REV3L with Rev7, which associates with Rev1), Pol ι (iota), Pol κ (kappa), and Rev1 (terminal deoxycytidyl transferase), *E. coli*, Pol IV (DINB) and PolV (UmuD'$_2$C)), or RT (e.g, RNA-dependent DNA polymerase, telomerase, HIV-1 reverse transcriptase, M-MLV reverse transcriptase, AMV reverse transcriptase). In some aspects the polymerase may be, for example, a DNA polymerase such as for example DNA polymerase, DNA polymerasae I-V, Taq Polymerase, Tfl (*Thermus flavus*) DNA polymerase, Tth (*Thermus thermophilus*) DNA polymerase, and Pfu (*Pyrococcus furiosus*) DNA polymerase. In some aspects, the reverse transcriptase can be, for example, reverse transcriptase, ImProm-II™ Reverse Transcriptase, GoScript™ Reverse Transcriptase, AMV Reverse Transcriptase, or M-MLV Reverse Transcriptase.

Some embodiments relate to methods of designing a nucleic acid amplification HotStart nucleic acids. The methods can include for example, performing at least one nucleic acid amplification in the presence of a sulfur containing oligo; and determining the amount of nonspecific product relative to a control nucleic acid amplification with no sulfur containing oligo. In some aspects at least two nucleic acid amplifications may be performed in the presence of sulfur containing oligos with different numbers of sulfur atoms; and determining the amount of nonspecific product produced relative to each other, for example.

Some embodiments relate to methods of reducing nonspecific products produced by reverse transcriptase and/or DNA polymerase. The methods can include, for example, contacting a reverse transcriptase or DNA polymerase with an oligonucleotide having from 5-50 nucleotides, wherein 40% -100% of said nucleotides include a sulfur atom.

Some embodiments relate to methods of reducing nonspecific products produced by DNA polymerase and reverse transcriptase. The methods may include, for example, contacting a mixture including DNA polymerase and reverse transcriptase with an oligonucleotide having from 5-50 nucleotides, wherein 40% -100% of said nucleotides comprise a sulfur atom.

Some embodiments relate to compositions or products that include, separately (e.g, two separate vials) or combined in a single composition or product, nucleic acid modifying enzyme and an oligonucleotide having from 5-50 nucleotides, wherein 40% -100% of said nucleotides include a sulfur atom.

Some embodiments relate to methods of nucleic acid amplification, which may include, for example, contacting any composition described herein with an amplification target sequence and at least one PCR primer specific for said amplification target sequence.

Some embodiments relate to molecules used as a hotstart for DNA polymerase. The molecules can be used, for example as a hotstart for reverse transcriptase. Preferably, the molecules are s-oligos of 5-50 nucleotides where 40% to about 100% of the nucleotides are modified to include at least one sulfur atom. Preferably, the oligonucleotides have from about 40% to 100% phosphorothioate linkages or phosphorodithioate linkages.

The molecules may include, for example, an oligonucleotide, deoxyribonucleic acids or a sulfur containing oligonucleotide. The sulfur can be, for example, part of a phosphorothioate or phosphorodithioate linkage.

Some embodiments relate to sticky oligonucleotides used as a hotstart for a polymerase. The polymerase can be, for example, a DNA polymerase, a reverse transcriptase or the like.

DETAILED DESCRIPTION

Definitions

Figure 1:
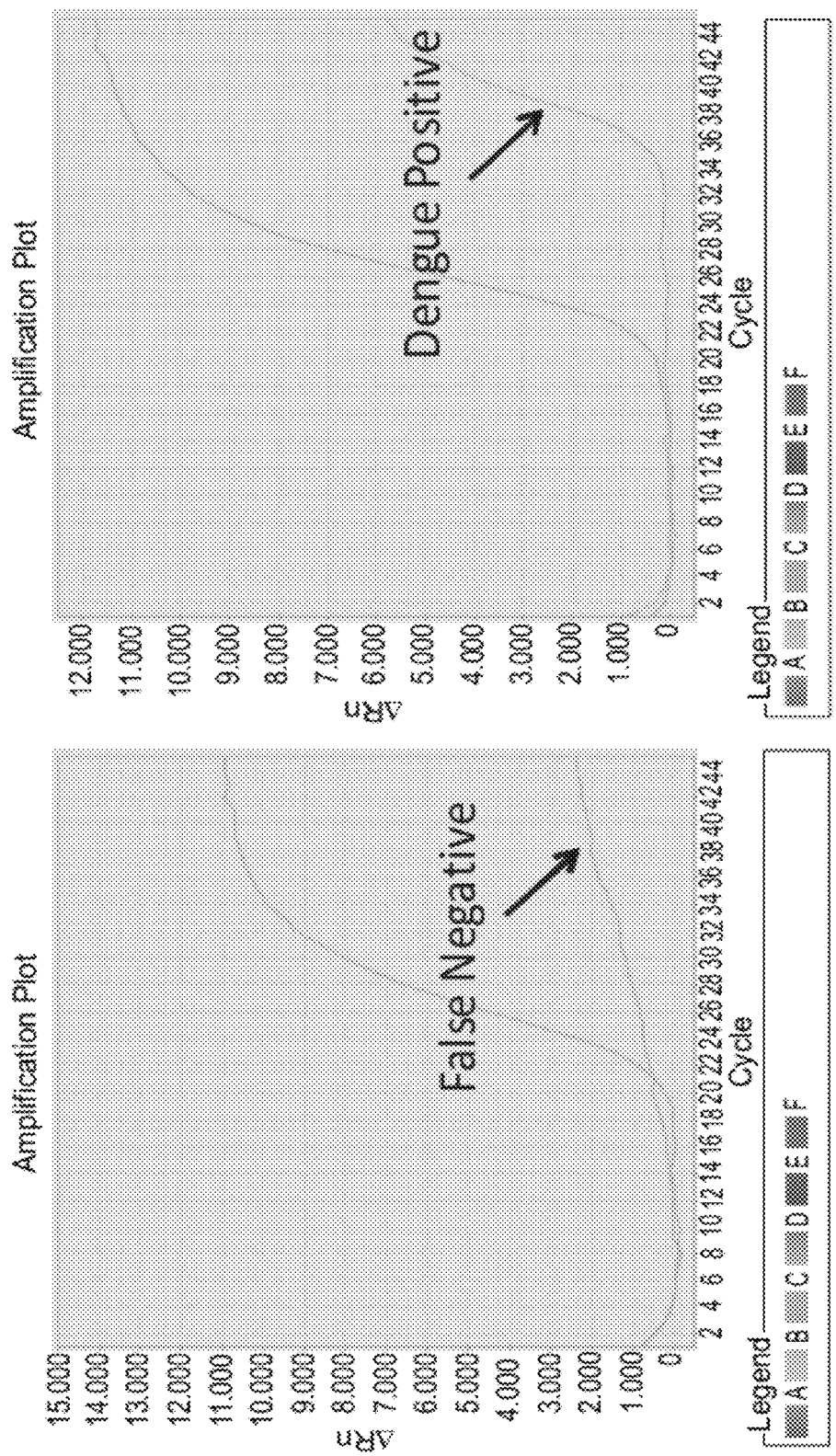
FIG. 1: Shows high concentration and low concentration positive controls in a Dengue RNA real-time PCR reaction without s-oligo hotstart (left) and with s-oligo hotstart (right). High concentration controls were detected by both assays, but false negatives were experienced by the assay with no hotstart due to the room temperature activity of the reverse transcriptase. Addition of the s-oligo eliminated false negatives due to primer depletion caused by room temperature nonspecific extension by the reverse transcriptase.

Amplicon—the amplicon is the product of a nucleic acid amplification reaction.

Amplification—Numerous methods of amplification of a nucleic acid are known to those skilled in the art. In general, the amplification of a nucleic acid sequence includes creating one or more copies of the nucleic acid sequence or of a secondary nucleic acid sequence intended to be indicative of the presence of the first nucleic acid. Examples include, but are not limited to polymerase chain reaction (PCR), rolling circle amplification (RCA), nucleic acid sequence based amplification (NASBA), transcription mediated amplification (TMA), ligase chain reaction (LCR), loop-mediated isothermal amplification (LAMP), among others.

Contiguous bases—contiguous bases refers to a series of nucleic acid bases. For the purpose of this application, mismatches, deletions or insertions do not interrupt the series of "contiguous bases." Some embodiments herein relate to oligonucleotides having 6 or more contiguous bases from any sequence described herein.

Detect—To detect a given target means to observe the change in signal due to the presence of the target and may include qualitative or quantitative analysis.

HotStart—a technique or modification to an enzyme that reduces enzymatic activity at or below room temperature (25C), but that reduces enzymatic activity to a lesser degree at the reaction temperature, which is above room temperature.

Oligonucleotide—oligonucleotide is a sequence of natural and/or modified bases of between about 5 and 1000 bases, 10 and 200 bases, 10 and 50 bases.

Polymerase—a naturally occurring, modified or de novo enzyme with the ability to add bases to a primer. Examples of polymerase include, but are not limited to, DNA polymerases, RNA polymerases and reverse transcriptases. A variety of DNA polymerases are known to those skilled in the art and include but are not limited to Taq polymerase, Vent polymerase, Pfu polymerase, Bst polymerase, Tfl polymerase, Tth DNA polymerase, Tsp polymerase, Pfx polymerase, T4 DNA polymerase, T7 DNA polymerase, Bsu DNA polymerase, phi29 DNA polymerase, DNA polymerase I. A variety of RNA polymerases are known to those skilled in the art including, but not limited to, phi6 RNA polymerase, SP6 RNA polymerase, T3 RNA polymerase, T7 RNA polymerase. A variety of reverse transcriptases are known to those skilled in the art including, but not limited to, AMV reverse transcriptase, MLV reverse transcriptase, M-MuLV reverse transcriptase, HIV reverse transcriptase. There are also a variety of recombinant and modified versions of these and other polymerases known to those skilled in the art.

Primer—a primer is an oligonucleotide used to prime or initiate a nucleic acid extension reaction, which also includes priming the extension in nucleic acid amplification reactions.

Probe—a probe is an oligonucleotide that is used to detect the presence of a nucleic acid sequence.

S-oligo—an oligonucleotide that contains at least one phosphorothioate linkage. Some embodiments disclosed herein relate to the surprising discovery of the use of S-oligos in temperature dependent reactions, such as for example, reactions using nucleic acid modifying enzymes; for example, PCR or RT PCR.

While s-oligos are mentioned herein, it should be understood that many other nucleic acid analogs and/or modified bases may be substituted and utilized in the methods described herein. Examples of such analogs or modified bases with sulfur atoms include, without being limited thereto, 6-Thio-2'-deoxyguanosine, 4-Thiothymidine, 2-Thiothymidine, 4-Thio-2'-deoxyuridine, phosphorothioate and phosphorodithioate linkages. And examples of such analogs or modified bases without sulfur atoms include, without being limited thereto, 8-Bromo-2'-deoxyadenosine, 8-Bromo-2'-deoxyguanosine, 7-Deaza-2'-deoxyadenosine, 7-Deaza-2'-deoxyguanosine, 7-Deaza-2'-deoxyxanthosine, 2,6-Diaminopurine-2'-deoxyriboside, Etheno-2'-deoxyadenosine, N6-Methyl-2'-deoxyadenosine, O6-Methyl-2'-deoxyguanosine, O6-Phenyl-2'-deoxyinosine, 8-Oxo-2'-deoxyadenosine, 8-Oxo-2'-deoxyguanosine, C4-(1,2,4-Triazol-1-yl)-2'-deoxyuridine, 6-O-(TMP)-5-F-2'-deoxyuridine, 5-Propynyl-2'-deoxyuridine, 5-Propynyl-2'-deoxycytidine, O4-Methylthymidine, 5-Methyl-2'-deoxycytidine, 5-Iodo-2'-deoxyuridine, 5-Iodo-2'-deoxycytidine, 5-Hydroxy-2'-deoxyuridine, 5-Hydroxymethyl-2'-deoxyuridine, 5-Fluoro-2'-deoxyuridine, N4-Ethyl-2'-deoxycytidine, 5,6-Dihydro-2'-deoxyuridine, 5,6-Dihydrothymidine, 2'-Deoxyuridine, 2'-Deoxypseudouridine, 5-(Carboxy)vinyl-2'-deoxyuridine, 5-Bromo-2'-deoxyuridine, 5-Bromo-2'-deoxycytidine, 5'-Aminothymidine, 2-Aminopurine, 5-Bromouridine, 2,6-Diaminopurine, Inosine, 5-Iodouridine, 5-Methylcytidine, 5-Methyluridine, Puromycin, 4-Thiouridine, 2-Aminopurine-2'-deoxyriboside, 2'-Deoxyinosine, 2'-Deoxyisoguanosine, 2'-Deoxynebularine, K-2'-deoxyribose (5' or Internal), 5-Nitroindole-2'-deoxyriboside (5' or Internal), 3-Nitropyrrole-2'-deoxyriboside (5' or Internal), P-2'-deoxyribose (5' or Internal), 2-Aminopurine-2'-O-methylriboside, 5-Bromo-2'-O-methyluridine, 3-Deaza-5-aza-2'-O-methylcytidine, 2,6-Diaminopurine-2'-O-methylriboside, 5-Fluoro-2'-O-methyluridine, 5-Fluoro-4-O-TMP-2'-O-methyluridine, 2'-O-Methylinosine, 5-Methyl-2'-O-methylcytidine, 5-Methyl-2'-O-methylthymidine, 8-Amino-2'-deoxyadenosine, 8-Amino-2'-deoxyguanosine, 7-Deaza-8-aza-2'-deoxyadenosine, 2,4-Difluorotoluyl, 5-(C2-EDTA)-2'-deoxyuridine, 5-Hydroxy-2'-deoxycytidine, Pyrrolo-2'-deoxycytidine, Thymidine Glycol, Pyrrolocytidine, K-2'-deoxyribose (3'), 5-Methyl-2'-Deoxyisocytidine, P-2'-deoxyribose (3'), 3'-Deoxyadenosine, 3'-Deoxycytidine, 3'-Deoxyguanosine, 3'-Deoxythymidine, 2', 3'-Dideoxyadenosine, 2',3'-Dideoxycytidine, 2',3'-Dideoxyguanosine, 2',3'-Dideoxythymidine, 5'-Iodothymidine, 5-O-Methylthymidine, Aracytidine, peptide nucleic acids, locked nucleic acids, and other modified bases.

Sticky oligonucleotide—A "sticky oligonucleotide" is an oligonucleotide comprised of modified nucleic acid bases or linkages that possess a nonspecific affinity for proteins, such that any inhibitory effect for the polymerase is determined by the number of modified bases and/or linkages in a sequence independent manner. The affinity of the oligonucleotide for the polymerase and its corresponding inhibitory effect is a function of the number of sticky bases/linkages. "Sticky oligonucleotides" may be combined with a specific sequence that confers greater affinity for the polymerase, such as an aptamer. Examples of nonspecifically "sticky oligonucleotides" include but are not limited to oligos with phosphorothioate linkages and phosphorodithioate linkages.

Sulfur containing oligonucleotide—an oligonucleotide containing at least one sulfur molecule. Examples of sulfur containing oligonucleotides include, but are not limited to oligos with phosphorothioate and phosphorodithioate linkages. S-oligos are examples of "sulfur containing oligonucleotides."

Some embodiments relate to methods of developing or designing oligonucleotides for use in temperature dependent reactions. In some aspects, the development of sticky oligonucleotides with temperature dependent inhibition polymerases may be accomplished through a series of optimization steps, including those illustrated herein, for example. In a preferred embodiment, an s-oligo is used that is either a homopolymer or a heteropolymer. In some embodiments an s-oligo that is inert relative to other reagents, such as primers, is desired. In some embodiments, an inert s-oligo might comprise or consist of a series of adenines. In other embodiments, a stronger affinity with the enzyme is desired and GC content may be used to increase the affinity of the s-oligo for the polymerase. Also, in some aspects, the oligonucleotide may be designed so that it is not complementary to the amplicon or to the target sequence, but instead so that it has non-specific affinity for a nucleic acid modifying enzyme, such as a polymerase or reverse transcriptase. In some embodiments, the modified bases contributing to a decrease in nonspecific activity of the enzyme can be part of the primer or probe, which can result in reducing the number of oligos in the reaction. In other embodiments modified bases do not comprise part of the primer or probe. In still other embodiments, the modified oligos the provide the hotstart functionality are not substantially complementary to an amplification product. For example, such modified oligos can have less than about 20, about 15, about 10, about 5 contiguous complementary bases to an amplification product.

In some embodiments, the temperature dependent inhibition can be controlled by the number of phosphorothioate linkages in the s-oligo. In some aspects, the number of phosphorothioate linkages can be used to control inhibition more than by the sequence of the s-oligo. The affinity and corresponding inhibition temperature range generally increase with the number of phosphorothioate linkages present in the oligo. In some embodiments, at least about 5, 10, or 15 phosphorothioate linkages are used to increase the affinity of the oligo for the enzyme.

In preferred embodiments, the nucleic acid modifying enzyme can be a polymerase, for example, a DNA polymerase, an RNA polymerase or a reverse transcriptase. Other In a preferred embodiment, a maximum degree of inhibition is desired at lower temperatures while retaining full activity of the enzyme at the reaction temperature. In some embodiments, various lengths of s-oligos are synthesized from about 5 bases to about 50, from about 10 to about 30, from about 15 to about 25 bases. The degree of substitution with sulfur or other atoms can range, for example, from about 40% to 100%. Preferably, in some embodiments the oligonucleotides can have from about 40% to about 100% phosphorothioate linkages. In some embodiments the sequence is a poly-A, a poly-T or a poly-AT sequence to avoid interactions with other molecules in the reaction.

In still other embodiments, each different length of possible s-oligo hotstart oligonucleotides is added in varying concentrations to an enzymatic reaction. In preferred embodiments the final concentration of s-oligo is between about 1 nM and 10 µM, 10 nM and 2 µM, 50 nM and 1 µM.

In yet other embodiments, each concentration of oligo at different lengths is evaluated for inhibition of the enzymatic reaction at the reaction temperature. In one embodiment the method for evaluating inhibition is to perform the reaction at the reaction temperature and measure the output in comparison with a control with no s-oligo present. In some embodiments, the longest s-oligo at the highest concentration that allows the enzymatic reaction to proceed without inhibition is the optimal s-oligo at the optimum concentration.

In preferred embodiments, a 3' cap, such as a carbon chain, a PEG chain or numerous other chemical moieties known to those skilled in the art, is added to the S-oligo to prevent extension by a polymerase.

In some embodiments, a HotStart is made for more than one enzyme in a single reaction. In some embodiments, a single s-oligo is optimized to create a hotstart for both the reverse transcriptase and the DNA polymerase in a single step RT-PCR reaction.

In a preferred embodiment, the s-oligo is optimized for the enzyme with the lowest reaction temperature. In some embodiments, the enzyme with the lowest reaction temperature is the reverse transcriptase.

In some embodiments a phosphorodithioate linker is used as the sticky oligo component. In some embodiments this additional sulfur group increases the affinity for the polymerase relative to a phosphorothioate linkage. In some embodiments, the increased affinity for the polymerase requires a shorter oligonucleotide sequence to be used between about 5 and 50 bases, between about 5 and 30 bases, between about 5 and 20 bases.

EXAMPLE I

S-oligo Hotstart For Reverse Transcriptase in a Dengue Real-time PCR Reaction

The utility of the s-oligo hotstart method for reverse transcriptase was demonstrated through a Dengue real-time PCR assay. The Dengue assay consisted of Simplex RNA Master Mix (Cooperative Diagnostics, Cat # S1002) and 400 nM forward (GGAAGCTGTACGCGACTAGTGGTTA-GAGGA; SEQ ID NO:1) and reverse (CTGTGCCTG-GAGAGACAGCAGGA; SEQ ID NO:2) primer and 500 nM Rapid Probe ([6FAM] ACAGCATATTGACGCTGGGAAA-GACCAGA gcgtca [DABC]; SEQ ID NO:3). The s-oligo hotstart was created by adding the 19 base s-oligo A*A*A*A*A*A*A*A*A*A*A*A*A*A*A*A*A*A*A/3Phosph/(SEQ ID NO:4; each * represents a phosphorothioate linkage, the /3Phosph/ is a phosphate group added to the 3' end of the oligo) to a final concentration of 200 nM prior to adding the Dengue oligo mix and mixing well. 5 µL of each Dengue assay (with and without s-oligo hotstart) and 5 µL of high (200 fM) and low concentration (200 aM) Dengue nucleic acid were placed in an AB StepOne real-time PCR machine with a 10 min RT step at 55° C. followed by a 20 s denature step at 95° C. and 45 cycles of 1 s at 95° C. and 20 s at 55° C. Fluorescence was monitored in the FAM channel.

Figure 2:
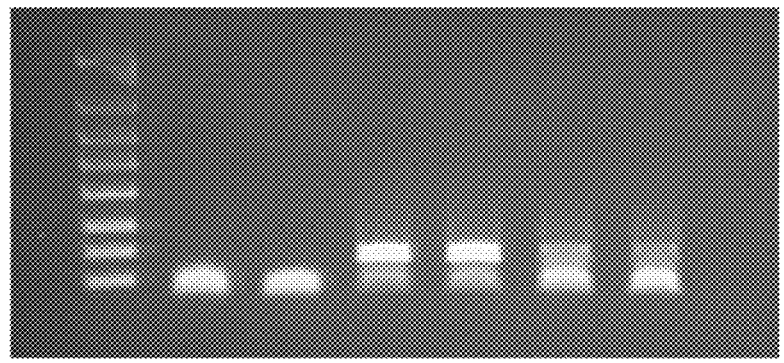
FIG. 2: Shows gel of Dengue reverse transcriptase PCR results using cDNA as a template. The first lane contains a ladder. Lanes 2 and 3 are negative controls with no RT present showing primer dimer formation. Lanes 4 and 5 are positive controls with no RT and show clear product formation. Lanes 6 and 7 are the same concentration of Dengue cDNA, but with RT present. The presence of RT clearly reduces product formation and increases primer-dimer formation.

The assay without any s-oligo hotstart was able to reliably detect the high concentration of Dengue nucleic acids (FIG. 1). However, it experienced repeated false negatives at the low concentration. The reverse transcriptase was determined to be the source of the problem by running the test with a synthetic DNA of the Dengue amplicon with and without RT (FIG. 2). When run without RT (i.e., using the Simplex DNA master mix (Cooperative Diagnostics, Cat # S1001)), the test detected all concentrations equally well. However, in the presence of the RT, false negative results were seen for the lower concentrations.

The test with the s-oligo hotstart did not have any false negatives from the low concentration Dengue nucleic acid, even after repeating the test multiple times. This demonstrates the first ever hotstart for a reverse transcriptase. It also demonstrates that the hotstart is capable of reducing primer extension by the reverse transcriptase at low temperatures, preventing false negatives caused by primer depletion.

EXAMPLE II

S-oligo Hotstart for DNA Polymerase in a Syphilis Real-time PCR Reaction

The utility of the s-oligo hotstart method for DNA polymerase was demonstrated through a *T. pallidum* (Syphilis) real-time PCR assay. The Syphilis assay consisted of Simplex DNA Master Mix (Cooperative Diagnostics, Cat # S1001) and 400 nM forward (GCGGTGAGGGGAATGTCTA; SEQ ID NO:5) and reverse (CAGCAAACGTTGACTTAAAAT-CAGGA; SEQ ID NO:6) primer and 500 nM Rapid Probe ([6FAM] AGAGGCAACCCTGCACTGTTATGGGGC-CTACCTggttgcc [DABC]; SEQ ID NO:7). The s-oligo hotstart was created by adding the 19 base s-oligo T*A*C*C*G*C*C*G*C*C*G*C*T*C*G*T*T*C*A/3Phosph/(SEQ ID NO:8; each * represents a phosphorothioate linkage, the /3Phosph/ is a phosphate group added to the 3' end of the oligo) to a final concentration of 200 nM prior to adding the Syphilis oligos and mixing well. 5 µL of each Syphilis assay (with and without s-oligo hotstart) and 5 µL of positive (200 fM) and negative (nuclease free water) controls were placed in an AB StepOne real-time PCR machine with a 20 s denature step at 95° C. and 45 cycles of 1 s at 95° C. and 20 s at 55° C. Fluorescence was monitored in the FAM channel.

Figure 3:
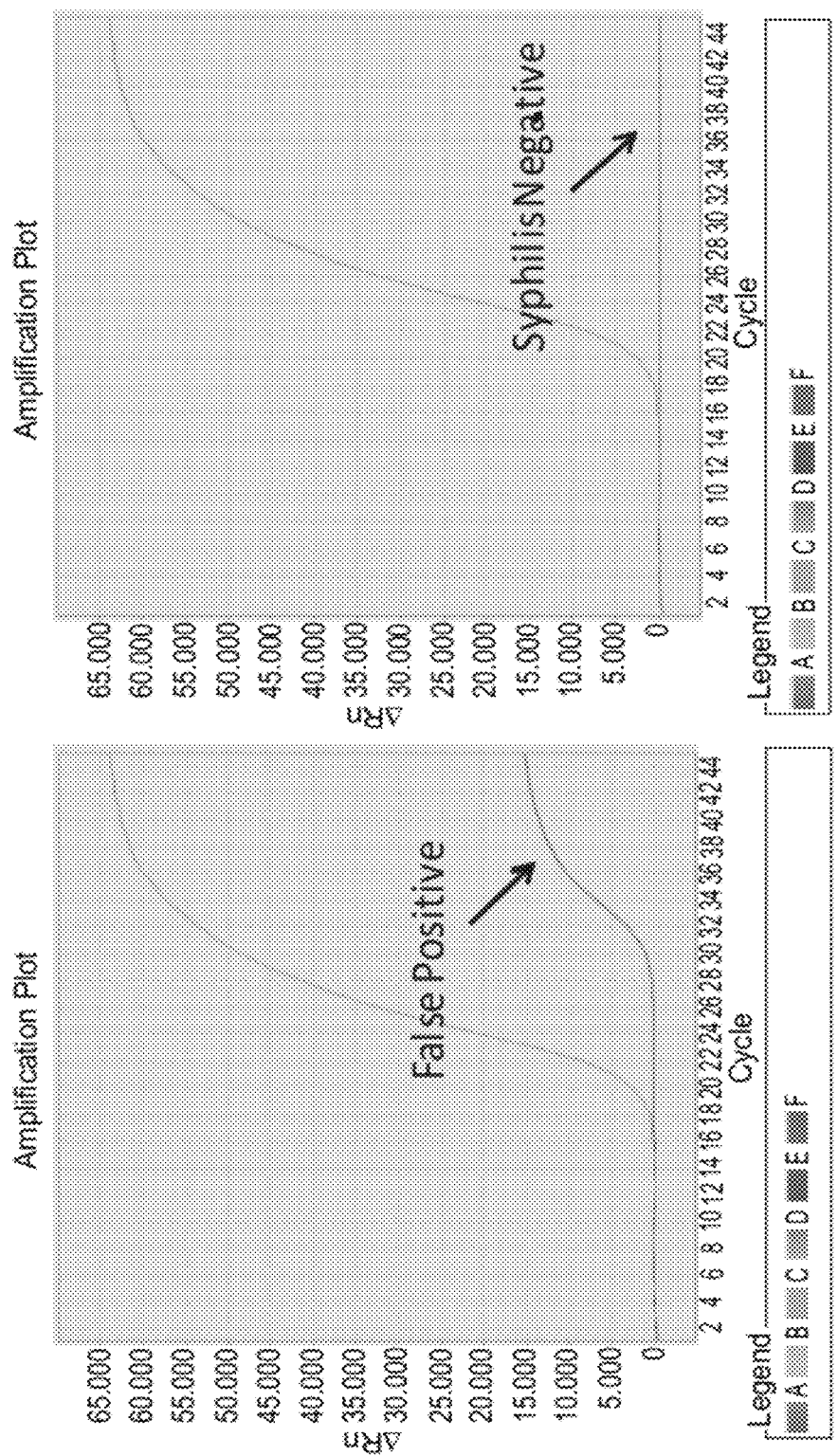
FIG. 3: Shows positive and negative controls in a *T. pallidum* DNA real-time PCR reaction without s-oligo hotstart (left) and with s-oligo hotstart (right). Addition of the s-oligo removed false positives from primer-dimers caused by room temperature activity of the Taq polymerase.

The assay without any s-oligo hotstart was able to reliably detect the positive control (FIG. 3). However, it experienced frequent false positives in the negative control. The false positives were caused by low temperature interaction of the polymerase with the primers and probe.

The test with the s-oligo hotstart did not have any false positives in the negative control and detected the positive control equally well, even after repeating the test multiple times. This demonstrates the first ever hotstart for a DNA polymerase using an s-oligo for temperature dependent inhibition of the enzyme. It also demonstrates that the hotstart is capable of reducing primer-dimers formed by the polymerase at low temperatures, preventing false positives.

EXAMPLE III

Selection of a Hotstart For DNA Taq Polymerase From Poly-A Oligos with 100% Phosphorothioate Linkages (XMRV)

S-oligos using poly-A sequences (17, 19, 21, 23, and 25 bases) with 100% phosphorothioate linkages were suspended at a 100 nM final concentration in Simplex DNA Master Mix [Cat.# S1001, Cooperative Diagnostics, Greenwood, S.C.], a 500 nM primer pair (Forward sequence: ACTGTG-GCAAATGGGGATGT (SEQ ID NO:9) and Reverse sequence: TGGAGACCGAGGAATCATAACA; SEQ ID NO:10), a 400 nM probe [6FAM] ATCATGGGAC-CTAATTTCCCTTAAGCGAGGAAACACTC- CTAGGTCCCAT [DABC] (SEQ ID NO:11), and either 5 μl water or 5 μl 20 aM DNA sequence: 5' TACTGTGCAAATGGGGATGTGAGACCACTGGA-CAGGCATACTGGAAGCCATCA TCATCATGGGAC-CTAATTTCCCTTAAGCGAGGAAACACTCCTAAGG ATCAGGGCC CCTGTTATGATTCCTCGGTCTC-CAGTGGCGTCCAGGGTGCCACACCGGGGGGTCG ATGCAACCCCCTGGTCTTAGAATTC 3' (SEQ ID NO:12) with a 10 μL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25A may be preferred in some embodiments as a hotstart oligonucleotide in this example:

| PolyA S-oligo length | Cycle threshold | ΔRn |
|---|---|---|
| 17A (SEQ ID NO: 13) | 32 | 3000 |
| 19A (SEQ ID NO: 4) | 32 | 4000 |
| 21A (SEQ ID NO: 14) | 31 | 7500 |
| 23A (SEQ ID NO: 15) | 32 | 5500 |
| 25A (SEQ ID NO: 16) | 32 | 5500 |

EXAMPLE IV

Selection of a Hotstart for DNA Taq Polymerase from Poly-A Oligos With 100% Phosphorothioate Linkages (Syphilis)

S-oligos using poly-A sequences (17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GCGGTGAGGG-GAATGTCTA (SEQ ID NO:5) and Reverse sequence: CAG-CAAACGTTGACTTAAAATCAGGA; SEQ ID NO:6), a 400 nM probe [6FAM] AGAGGCAACCCTGCACTGT-TATGGGGCCTACCTGGTTGCC [DABC] (SEQ ID NO:7), and either 5 μl water or 5 μl 20 aM DNA sequence:

5'GTTCCCCATTGTGGCAAAGAAG-GATTTCAAGTACCGCGGTGA GGGGAATGTCTAT-CACGAAGGGTTCTGCAAAGACGATAGAG-GCAACCCTGCACT GTTATGGGGCCTACCTGACCATTGGGAA-GAATCCTGATTTTAAGTCAACGTTTGC TGTTTTGTGGGAGTCTAAGG-GAGATAAGCCGGTGTATGAGCCGGGGTTT3' (SEQ ID NO:17) with a 10 μL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25A may be preferred in some embodiments as a hotstart oligonucleotide in this example:

| PolyA S-oligo length | Cycle threshold | ΔRn |
|---|---|---|
| 17A | 34 | 35000 |
| 19A | 34 | 37000 |
| 21A | 35 | 41000 |
| 23A | 35 | 32000 |
| 25A | 33 | 50000 |

EXAMPLE V

Selection of a Hotstart for DNA Taq Polymerase from Poly-A Oligos with 50% Phosphorothioate Linkages (Syphilis)

S-oligos using poly-A sequences (34, 38, 42, and 46 bases) with 50% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GCGGTGAGGGGAAT-GTCTA (SEQ ID NO:5) and Reverse sequence: CAG-CAAACGTTGACTTAAAATCAGGA; SEQ ID NO:6), a 400 nM probe [6FAM] AGAGGCAACCCTGCACTGT-TATGGGGCCTACCTGGTTGCC [DABC] (SEQ ID NO:7), and either 5 μl water or 5 μl 20 aM DNA sequence: 5'GTTC-CCCATTGTGGCAAAGAAGGATTTCAAG-TACCGCGGTGAGGGGAATGTCT ATCACGAAGGGT-TCTGCAAAGACGATAGAGGCAACCCTGCACTGTT ATGGGGCCT ACCTGACCATTGGGAAGAATCCT-GATTTTAAGTCAACGTTTGCTGTTTTGTGGGA GTCTAAGGGAGATAAGCCGGTGTAT-GAGCCGGGGTTT3' (SEQ ID NO:17) with a 10 μL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 46AA may be preferred in some embodiments as a hotstart oligonucleotide in this example:

| PolyA S-oligo length | Cycle threshold | ΔRn |
|---|---|---|
| 34AA (SEQ ID NO: 18) | 35 | 35000 |
| 38AA (SEQ ID NO: 19) | 32 | 57000 |
| 42AA (SEQ ID NO: 20) | 34 | 39000 |
| 46AA (SEQ ID NO: 21) | 35 | 41000 |

EXAMPLE VI

Selection of a Hotstart for DNA Tag Polymerase from Poly-AT Oligos with 100% Phosphorothioate Linkages (Syphilis)

S-oligos using poly-AT sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GCG-GTGAGGGGAATGTCTA (SEQ ID NO:5) and Reverse sequence: CAGCAAACGTTGACTTAAAATCAGGA; SEQ ID NO:6), a 400 nM probe [6FAM] AGAGGCAACCCTG-CACTGTTATGGGGCCTACCTGGTTGCC [DABC] (SEQ ID NO:7), and either 5 µl water or 5 µl 20 aM DNA sequence: 5'GTTCCCCATTGTGGCAAAGAAG-GATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25AT may be preferred in some embodiments as a hotstart oligonucleotide in this example:

| PolyAT S-oligo length | Cycle threshold | ΔRn |
|---|---|---|
| 17AT (SEQ ID NO: 22) | 32 | 46000 |
| 19AT (SEQ ID NO: 23) | 34 | 56000 |
| 21AT (SEQ ID NO: 24) | 31 | 45000 |
| 23AT (SEQ ID NO: 25) | 32 | 65000 |
| 25AT (SEQ ID NO: 26) | 32 | 58000 |

EXAMPLE VII

Selection of a Hotstart for DNA Taq Polymerase from Poly-AT Oligos with 100% Phosphorothioate Linkages (xmrv)

S-oligos using poly-AT sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: ACTGTGGCAAATGGGGATGT (SEQ ID NO:9) and Reverse sequence: TGGAGACCGAGGAATCATAACA; SEQ ID NO:10), a 400 nM probe [6FAM] ATCATGGGAC-CTAATTTCCCTTAAGCGAGGAAACACTC-CTAGGTCCCAT [DABC] (SEQ ID NO:11), and either 5 µl water or 5 µl 20 aM DNA sequence: 5' TACTGTG-GCAAATGGGGATGTGAGACCACTGGA-CAGGCATACTGGAAGCCATCA TCATCATGGGAC-CTAATTTCCCTTAAGCGAGGAAACACTCCTAA GGATCAGGGCC CCTGTTATGATTCCTCGGTCTC-CAGTGGCGTCCAGGGTGCCACACCGGGGGGTCG ATGCAACCCCCTGGTCTTAGAATTC 3' (SEQ ID NO:12) with a 10 µL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25AT may be preferred in some embodiments as a hotstart oligonucleotide in this example:

| PolyAT S-oligo length | Cycle threshold | ΔRn |
|---|---|---|
| 17AT | 34 | 5000 |
| 19AT | 35 | 12000 |
| 21AT | 34 | 21000 |
| 23AT | 34 | 20500 |
| 25AT | 35 | 27000 |

EXAMPLE VIII

Selection of a Hotstart for DNA Taq Polymerase from Poly-ACTG Oligos with 100% Phosphorothioate Linkages (Syphilis)

S-oligos using poly-ACTG sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GCG-GTGAGGGGAATGTCTA (SEQ ID NO:5) and Reverse sequence: CAGCAAACGTTGACTTAAAATCAGGA; SEQ ID NO:6), a 400 nM probe [6FAM] AGAGGCAACCCTG-CACTGTTATGGGGCCTACCTGGTTGCC [DABC] (SEQ ID NO:7), and either 5 µl water or 5 µl 20 aM DNA sequence: 5' GTTCCCCATTGTGGCAAAGAAG-GATTTCAAGTACCGCGGTGAGGGGAATGTCTAT CACGAAGGGTTCTGCAAAGACGATAGAG-GCAACCCTGCACTGTTATGGGGCCTAC CTGACCAT-TGGGAAGAATCCTGATTTTAAGT-CAACGTTTGCTGTTTTGTGGGAGT CTAAGGGAGATAAGCCGGTGTATGAGCCGGGGTTT 3' (SEQ ID NO:17) with a 10 µL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25ACTG may be preferred in some embodiments as a hotstart oligonucleotide in this example:

| PolyACTG S-oligo length | Cycle threshold | ΔRn |
|---|---|---|
| 17ACTG (SEQ ID NO: 27) | 32 | 60000 |
| 19ACTG (SEQ ID NO: 28) | 32 | 46000 |
| 21ACTG (SEQ ID NO: 29) | 33 | 51000 |
| 23ACTG (SEQ ID NO: 30) | 34 | 46000 |
| 25ACTG (SEQ ID NO: 31) | 32 | 58000 |

EXAMPLE IX

Selection of a Hotstart for DNA Taq Polymerase from Poly-ACTG Oligos with 100% Phosphorothioate Linkages (xmrv)

S-oligos using poly-ACTG sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: ACT-GTGGCAAATGGGGATGT (SEQ ID NO:9) and Reverse sequence: TGGAGACCGAGGAATCATAACA; SEQ ID NO:10), a 400 nM probe [6FAM] ATCATGGGAC- CTAATTTCCCTTAAGCGAGGAAACACTC-CTAGGTCCCAT [DABC] (SEQ ID NO:11), and either 5 μl water or 5 μl 20 aM DNA sequence: 5' TACTGTGGCAAATGGGGATGTGAGACCACTGGA-CAGGCATACTGGAAGCCATC ATCATCATGGGAC-CTAATTTCCCTTAAGCGAGGAAACACTCCTAA GGATCAGGGC CCCTGTTATGATTCCTCGGTCTC-CAGTGGCGTCCAGGGTGCCACACCGGGGGGTC GATGCAACCCCCTGGTCTTAGAATTC 3' (SEQ ID NO:12) with a 10 μL final volume. Runs were performed in replicates of two. PCR conditions were 20 s at 95° C. followed by 45 cycles of 1 s at 95° C., 20 s at 55° C. The largest s-oligo that did not delay the cycle threshold by more than 2 cycles, was selected as the optimal hotstart candidate for Taq polymerase in Simplex DNA Master Mix in a PCR with an annealing temperature of 55° C. Although not intending to be limited thereto, cycle thresholds and maximum fluorescence are shown for each positive sample and reveal that sequence 25ACTG may be preferred in some embodiments as a hotstart oligonucleotide in this example:

| PolyACTG S-oligo length | Cycle threshold | ΔRn |
|---|---|---|
| 17ACTG | 32 | 3500 |
| 19ACTG | 33 | 3500 |
| 21ACTG | 33 | 6000 |
| 23ACTG | 33 | 7000 |
| 25ACTG | 33 | 14000 |

EXAMPLE X

Figure 4:
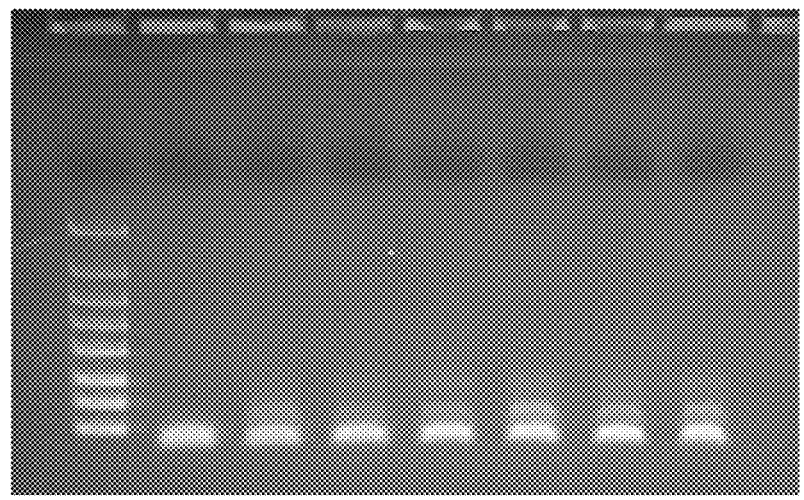
FIG. 4: Gel results of XMRV PCR with and without hotstart (100% phosphorothioate sequences from 17 to 25 poly-A bases). Description of gel picture reading left to right by lane (1) 100-4000 bp Flashgel® DNA Marker [CAT#50473, Lonza, Rockland, Me.], (2) Negative Control with 5 ul water, (3) Positive Control with 5 ul 20 aM DNA sequence, (4) 17A, (5) 19A, (6) 21A, (7) 23A, (8) 25A.

Selection of a Hotstart for Taq Polymerase from Poly-A Oligos with 100% Phosphorothioate Linkages (XMRV) Using Agarose Gel Electrophoresis S-oligos using poly-A sequences (17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: ACTGTGGCAAATGGGGATGT (SEQ ID NO:9) and Reverse sequence: TGGAGACCGAGGAATCATAACA; SEQ ID NO:10), a 400 nM probe [6FAM] ATCATGGGAC-CTAATTTCCCTTAAGCGAGGAAACACTC-CTAGGTCCCAT [DABC], (SEQ ID NO:11) and either 5 μl water or 5 μl 20 aM DNA sequence: 5' TACTGTGGCAAATGGGGATGTGAGACCACTGGA-CAGGCATACTGGAAGCCATCA TCATCATGGGAC-CTAATTTCCCTTAAGCGAGGAAACACTCCTAAG GATCAGGGCC CCTGTTATGATTCCTCGGTCTC-CAGTGGCGTCCAGGGTGCCACACCGGGGGGTCG ATGCAACCCCCTGGTCTTAGAATTC 3' (SEQ ID NO:12) with a 10 μL final volume. Runs were performed in replicates of two. PCR conditions were 20 s at 95° C. followed by 45 cycles of 1 s at 95° C., 20 s at 55° C. Agarose gel electrophoresis was performed on all PCR products using a 1.2% agarose gel. The largest s-oligo that had the greatest size product band and least primer dimer band was selected as the optimal hotstart candidate for Taq polymerase in GoTaq buffer in a PCR with an annealing temperature of 55° C. Product bands for each positive sample reveal that sequence 25A can be the preferred, but not limiting, hotstart in this example (FIG. 4).

EXAMPLE XI

Figure 5:
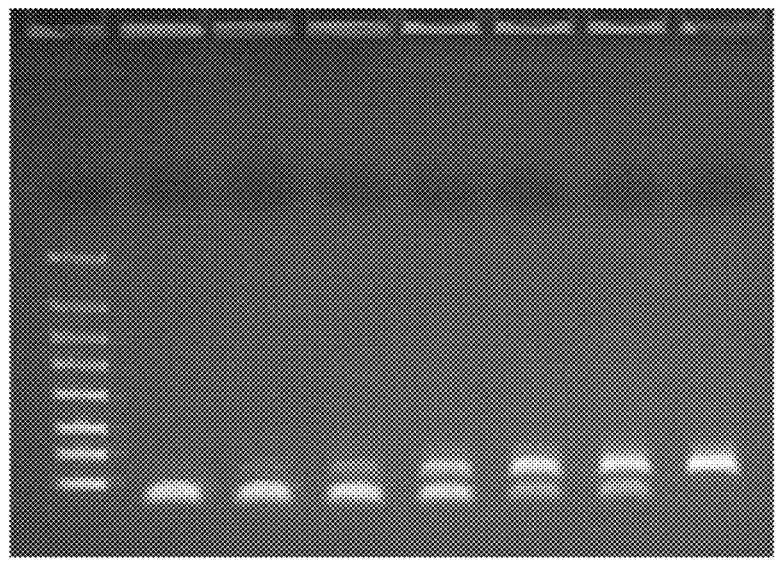
FIG. 5: Gel results of XMRV PCR with and without hotstart (100% phosphorothioate sequences from 17 to 25 poly-AT bases). Description of gel picture reading left to right by lane (1) 100-4000 bp Flashgel® DNA Marker [CAT#50473, Lonza, Rockland, Me.], (2) Negative Control with 5 ul water, (3) Positive Control with 5 ul 20 aM DNA sequence, (4) 17AT, (5) 19AT, (6) 21AT, (7) 23AT, (8) 25AT.

Selection of a Hotstart for Taq Polymerase from Poly-AT Oligos with 100% Phosphorothioate Linkages (xmrv) Using Agarose Gel Electrophoresis S-oligos using poly-AT sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: ACTGTGGCAAATGGGGATGT (SEQ ID NO:9) and Reverse sequence: TGGAGACCGAGGAATCATAACA; SEQ ID NO:10), a 400 nM probe [6FAM] ATCATGGGAC-CTAATTTCCCTTAAGCGAGGAAACACTC-CTAGGTCCCAT [DABC] (SEQ ID NO:11), and either 5 μl water or 5 μl 20 aM DNA sequence: 5' TACTGTGGCAAATGGGGATGTGAGACCACTGGA-CAGGCATACTGGAAGCCATCA TCATCATGGGAC-CTAATTTCCCTTAAGCGAGGAAACACTCCTAA GGATCAGGGCC CCTGTTATGATTCCTCGGTCTC-CAGTGGCGTCCAGGGTGCCACACCGGGGGGTCG ATGCAACCCCCTGGTCTTAGAATTC 3' (SEQ ID NO:12) with a 10 μL final volume. Runs were performed in replicates of two. PCR conditions were 20 s at 95° C. followed by 45 cycles of 1 s at 95° C., 20 s at 55° C. Agarose gel electrophoresis was performed on all PCR products using a 1.2% agarose gel. The largest s-oligo that had the greatest size product band and least primer dimer band was selected as the optimal hotstart candidate for Taq polymerase in GoTaq buffer in a PCR with an annealing temperature of 55° C. Product bands for each positive sample reveal that sequence 25AT can be the preferred, but not limiting, hotstart in this example (FIG. 5).

EXAMPLE XII

Selection of a Hotstart for Taq Polymerase from Poly-ACTG Oligos with 100% Phosphorothioate Linkages (xmrv) Using Agarose Gel Electrophoresis S-oligos using poly-ACTG sequences (15, 17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: ACTGTGGCAAATGGGGATGT (SEQ ID NO:9) and Reverse sequence: TGGAGACCGAGGAATCATAACA; SEQ ID NO:10), a 400 nM probe [6FAM] ATCATGGGAC-CTAATTTCCCTTAAGCGAGGAAACACTC-CTAGGTCCCAT [DABC] (SEQ ID NO:11), and either 5 μl water or 5 μl 20 aM DNA sequence: 5' TACTGTGGCAAATGGGGATGTGAGACCACTGGA-CAGGCATACTGGAAGCCATC ATCATCATGGGAC-CTAATTTCCCTTAAGCGAGGAAACACTCCTAAGG ATCAGGGC CCCTGTTATGATTCCTCGGTCTC-CAGTGGCGTCCAGGGTGCCACACCGGGGGGTC GATGCAACCCCCTGGTCTTAGAATTC 3' (SEQ ID NO:12) with a 10 μL final volume. Runs were performed in replicates of two. PCR conditions were 20 s at 95° C. followed by 45 cycles of 1 s at 95° C., at 55° C. Agarose gel electrophoresis was performed on all PCR products using a 1.2% agarose gel. The largest s-oligo that had the greatest size product band and least primer dimer band was selected as the optimal hotstart candidate for Taq polymerase in GoTaq buffer in a PCR with an annealing temperature of 55° C.

Figure 6:
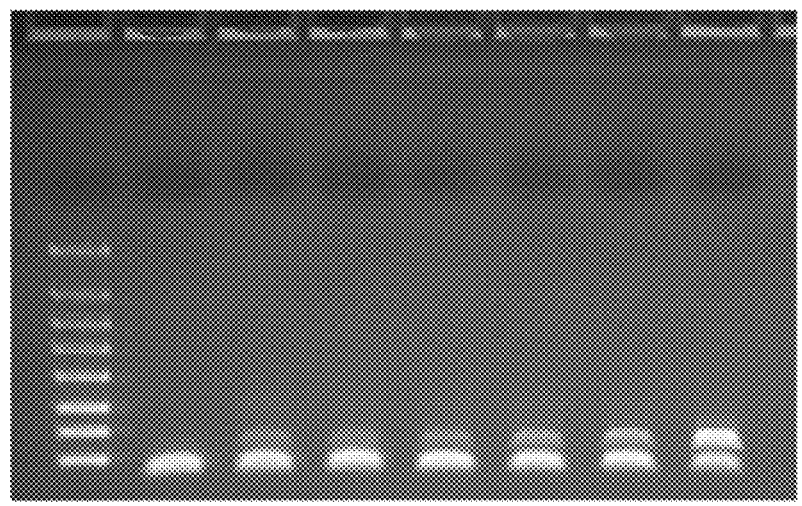
FIG. 6: Gel results of XMRV PCR with and without hotstart (100% phosphorothioate sequences from 17 to 25 poly-ACTG bases). Description of gel picture reading left to right by lane (1) 100-4000 bp Flashgel® DNA Marker [CAT#50473, Lonza, Rockland, Me.], (2) Negative Control with 5 ul water, (3) Positive Control with 5 ul 20 aM DNA sequence, (4) 17ACTG, (5) 19ACTG, (6) 21ACTG, (7) 23ACTG, (8) 25ACTG.

Product bands for each positive sample reveal that sequence 25ACTG can be the preferred, but not limiting, hotstart in this example (FIG. 6).

EXAMPLE XIII

Selection of a Hotstart for ImProm-II™ Reverse Transcriptase from Poly-A Oligos with 100% Phosphorothioate Linkages S-oligos using poly-A sequences (17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GGAAGCTG-TACGCGACTAGTGGTTAGAGGAGA (SEQ ID NO:32) and Reverse sequence: CTGTGCCTGGAGAGACAG-CAGGA; SEQ ID NO:2), a 400 nM probe [6FAM] ACAG-CATATTGACGCTGGGAAAGACCAGAGCGTCA [DABC] (SEQ ID NO:*), ImProm-II™ Reverse Transcriptase, and either 5 µl water or 5 µl 200 fM RNA sequence: 5'          GGAAGCTGTACGCGTGGCATATTGGAC-TAGCGGTTAGAGGAGACCCCTCCCACCA         CTGA-CAAAACGCAGCAAAAGGGGGCCCGAAGC-CAGGAGGAAGCTGTACTCCTGG TGGAAGGACTAGAGGTTAGAGGAGAC-CCCCCCAACACAAAAACAGCATATTGAC          GCTGG-GAAAGACCAGA 3' (SEQ ID NO:34) with a 10 µL final volume. Runs were performed in replicates of two. PCR conditions were 10 minutes at 55° C., 20 s at 95° C. followed by 45 cycles of 1 s at 95° C., 20 s at 60° C. The largest s-oligo that did not delay the cycle threshold by more than 2 cycles, was selected as the optimal hotstart candidate for ImProm-II™ Reverse Transcriptase in Simplex DNA Master Mix in a PCR with an annealing temperature of 60° C. Although not intending to be limited thereto, cycle thresholds and maximum fluorescence are shown for each positive sample and reveal that sequence 23A may be preferred in some embodiments as a hotstart oligonucleotide in this example:

| PolyA S-oligo length | Cycle threshold |
|---|---|
| No hotstart | 28 |
| 17A | 28 |
| 19A | 29 |
| 21A | 28 |
| 23A | 30 |
| 25A | 32 |

Figure 7:
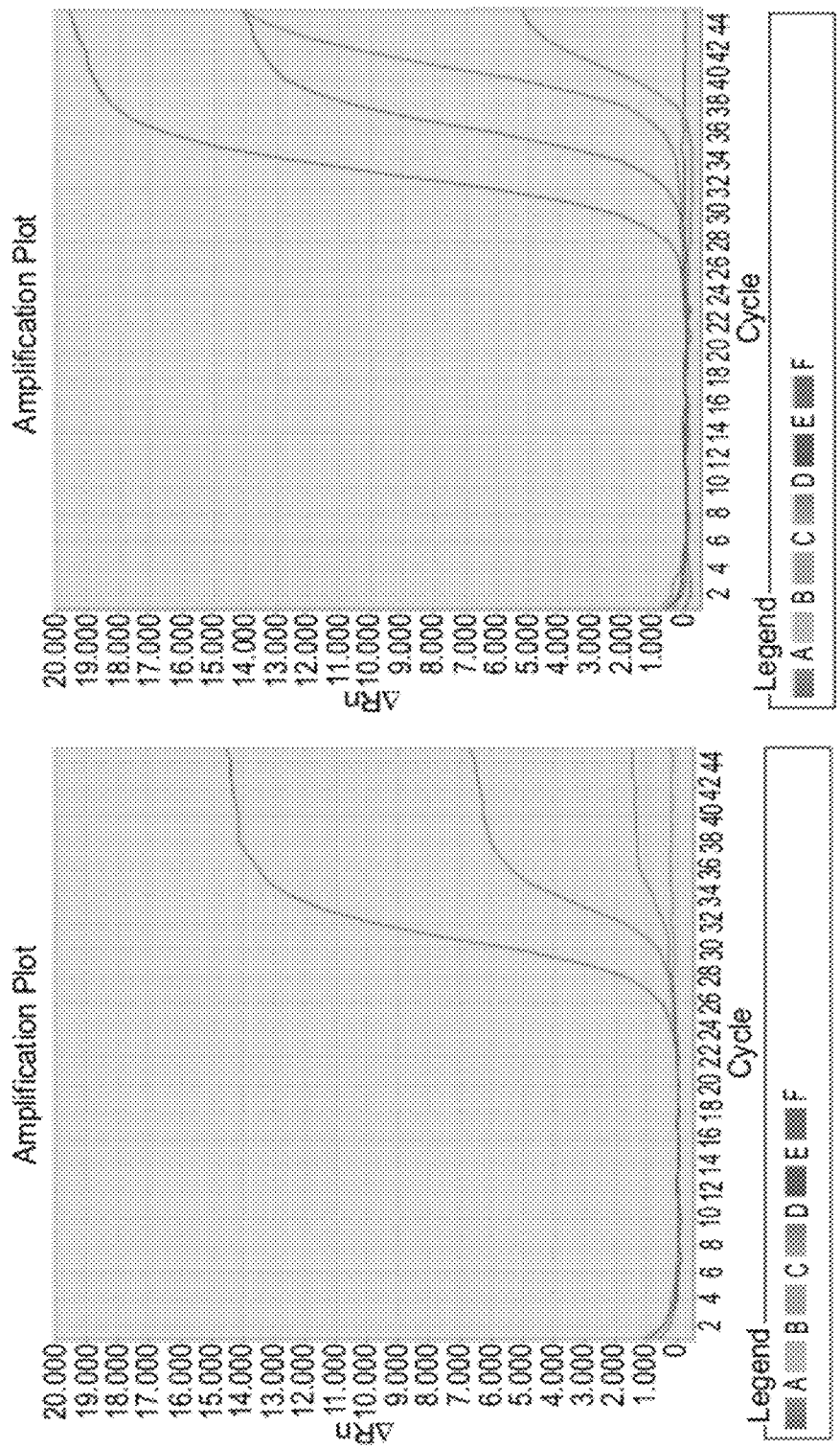
FIG. 7: Reverse transcriptase real-time PCR dilution series of Dengue RNA sequences with no hotstart (left) and with 23A hotstart (right). The no hotstart reaction experienced lower fluorescence values for even the highest concentration run. It had positives for 200 fM and 20 fM concentrations, but was not called positive by StepOne software for 2 fM or 200 aM concentrations. In contrast, the dilution series with hotstart had large fluorescence output. It was able to detect both the 2 fM and 200 aM dilutions, exhibiting a 100 fold increase in the detection limit.

Additionally, each of the hotstarts were used as described above, but with serial dilutions of Dengue RNA from 200 fM to 200 aM. The mix without hotstart could not detect anything below 20 fM. 17A had a slightly detectable signal at 2 fM. 19A had a slightly higher signal at 2 fM. 21A had a much higher signal at 2 fM. The 23A mix was able to detect the 200 aM concentration, a 100 fold improvement in the detection limit over the master mix with no hotstart (FIG. 7). 25A inhibited the RT too much and had no signal for 200 aM and only a slight signal for 2 fM.

Figure 8:
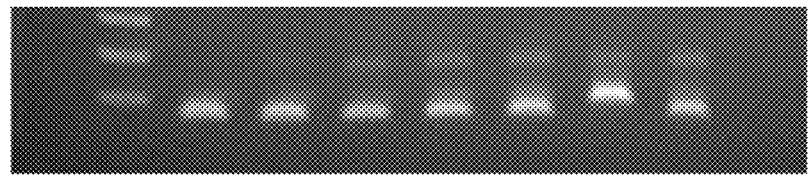
FIG. 8: Gel results of reverse transcriptase PCR with Dengue RNA sequences with and without hotstart (100% phosphorothioate sequences from 17 to 25 poly-A bases). Description of gel picture reading left to right by lane (1) 100-4000 bp Flashgel® DNA Marker [CAT#50473, Lonza, Rockland, Me.], (2) Negative Control with 5 ul water, (3) Positive Control with 5 ul 20 aM DNA sequence, (4) 17A, (5) 19A, (6) 21A, (7) 23A, (8) 25A. 23A produced a larger amount of product with no discernable primer-dimer band and was therefore selected as the optimal RT hotstart for this reaction.

A gel run on all 5 poly-A hotstart PCRs used in this experiment and a no hotstart control PCR showed that primer dimer was formed in all the reactions except for the reaction with 23A (FIG. 8). The 23A reaction also had the most amplicon visible. These results support the idea that in some non-limiting embodiments the largest s-oligo causing no more than a 2-cycle delay preferably may be used.

EXAMPLE XIV

Selection of a Hotstart for ImProm-II™ Reverse Transcriptase from Poly-AT Oligos with 100% Phosphorothioate Linkages S-oligos using poly-AT sequences (17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GGAAGCTG-TACGCGACTAGTGGTTAGAGGAGA (SEQ ID NO:32) and Reverse sequence: CTGTGCCTGGAGAGACAG-CAGGA; SEQ ID NO:2), a 400 nM probe [6FAM] ACAG-CATATTGACGCTGGGAAAGACCAGAGCGTCA [DABC] (SEQ ID NO:*), ImProm-II™ Reverse Transcriptase, and either 5 µl water or 5 µl 200 fM RNA sequence: 5'          GGAAGCTGTACGCGTGGCATATTGGAC-TAGCGGTTAGAGGAGACCCCTCCCACCA         CTGA-CAAAACGCAGCAAAAGGGGGCCCGAAGC-CAGGAGGAAGCTGTACTCCTGG TGGAAGGACTAGAGGTTAGAGGAGAC-CCCCCCAACACAAAAACAGCATATTGAC          GCTGG-GAAAGACCAGA 3' (SEQ ID NO:34) with a 10 µL final volume. Runs were performed in replicates of two. PCR conditions were 10 minutes at 55° C., 20 s at 95° C. followed by 45 cycles of 1 s at 95° C., 20 s at 60° C. The largest s-oligo that did not delay the cycle threshold by more than 2 cycles was selected as the optimal hotstart candidate for ImProm-II™ Reverse Transcriptase in Simplex DNA Master Mix in a PCR with an annealing temperature of 60° C. Although not intending to be limited thereto, cycle thresholds and maximum fluorescence are shown for each positive sample and reveal that sequences 17AT and 19AT may be preferred in some embodiments as a hotstart oligonucleotides in this example:

| Poly-AT oligo length | Cycle threshold |
|---|---|
| No HotStart | 28 |
| 17AT | 30 |
| 19AT | 30 |
| 21AT | 34 |
| 23AT | 35 |
| 25AT | 36 |

When dilution series were made and run with each hotstart, 17AT increased the sensitivity by 10 fold. 19AT was a little too inhibitory to improve the sensitivity much. Therefore, these results indicate that 17AT should be selected out of the two choices. The larger 25AT actually reduced the sensitivity by 10 fold.

EXAMPLE XV

Selection of a Hotstart for ImProm-II™ Reverse Transcriptase from Poly-ACTG Oligos with 100% Phosphorothioate Linkages S-oligos using poly-ACTG sequences (17, 19, 21, 23, and 25 bases) with 100% phosphorothioate linkages were suspended at a 100 nM final concentration in Simplex DNA Master Mix [Cat. # S1001, Cooperative Diagnostics, Greenwood, S.C.], a 500 nM primer pair (Forward sequence: GGAAGCTGTACGCGACTAGTGGTTAGAGGAGA (SEQ ID NO:32) and Reverse sequence: CTGTGCCTG-GAGAGACAGCAGGA; SEQ ID NO:2), a 400 nM probe

[6FAM] ACAGCATATTGACGCTGGGAAAGACCA-GAGCGTCA [DABC] (SEQ ID NO:*), ImProm-II™ Reverse Transcriptase, and either 5 µl water or 5 µl 200 fM RNA sequence: 5' GGAAGCTGTACGCGTGGCATATTG-GACTAGCGGTTAGAGGAGACCCCTCCCACCA CTGACAAAACGCAGCAAAAGGGGGC-CCGAAGCCAGGAGGAAGCTGTACTCCTGG TGGAAGGACTAGAGGTTAGAGGAGAC-CCCCCCAACACAAAAACAGCATATTGAC GCTGG-GAAAGACCAGA 3' (SEQ ID NO:34) with a 10 µL final volume. Runs were performed in replicates of two. PCR conditions were 10 minutes at 55° C., 20 s at 95° C. followed by 45 cycles of 1 s at 95° C., 20 s at 60° C. The largest s-oligo that did not delay the cycle threshold by more than 2 cycles, was selected as the optimal hotstart candidate for ImProm-II™ Reverse Transcriptase in Simplex DNA Master Mix in a PCR with an annealing temperature of 60° C. Cycle thresholds and maximum fluorescence are shown for each positive sample and reveal that in some embodiments shorter sequences than those tested may be preferred:

| PolyACTG S-oligo length | Cycle threshold |
|---|---|
| No HotStart | 28 |
| 17ACTG | 31 |
| 19ACTG | 32 |
| 21ACTG | 33 |
| 23ACTG | 34 |
| 25ACTG | 35 |

EXAMPLE XVI

Selection of a Hotstart for Tfl (*Thermus flavus*) DNA Polymerase from Poly-A Oligos with 100% Phosphorothioate Linkages S-oligos using poly-A sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGTTGACT-TAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tfl (*Thermus flavus*) DNA polymerase, and either 5 µl water or 5 µl 20 aM DNA sequence: 5'GTTCCCCATTGTGGCAAAGAAG-GATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT 3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the preferred hotstart candidate for Tfl (*Thermus flavus*) DNA polymerase in 2× Reaction Buffer in a PCR with an annealing temperature of 55° C.

EXAMPLE XVII

Selection of a Hotstart for Tfl (*Thermus flavus*) DNA Polymerase from Poly-A Oligos with 50% Phosphorothioate Linkages S-oligos using poly-A sequences (34-46 bases) with 50% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGTTGACT-TAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tfl (*Thermus flavus*) DNA polymerase, and either 5 µl water or 5 µl 20 aM DNA sequence: 5' GTTCCCCATTGTGGCAAAGAAG-GATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT 3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Tfl (*Thermus flavus*) DNA polymerase in 2× Reaction Buffer in a PCR with an annealing temperature of 55° C.

EXAMPLE XVIII

Selection of a Hotstart for Tfl (*Thermus flavus*) DNA Polymerase from Poly-AT Oligos with 100% Phosphorothioate Linkages S-oligos using poly-AT sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGT-TGACTTAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tfl (*Thermus flavus*) DNA polymerase, and either 5 µl water or 5 µl 20 aM DNA sequence: 5'GTTCCCCATTGTGGCAAAGAAG-GATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Tfl (*Thermus flavus*) DNA polymerase in 2× Reaction Buffer in a PCR with an annealing temperature of 55° C.

EXAMPLE XIX

Selection of a Hotstart for Tfl (*Thermus flavus*) DNA Polymerase from Poly-ACTG Oligos with 100% Phosphorothioate Linkages S-oligos using poly-ACTG sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGT- TGACTTAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tfl (*Thermus flavus*) DNA polymerase, and either 5 µl water or 5 µl 20 aM DNA sequence: 5'GTTCCCCATTGTGGCAAAGAAG-GATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Tfl (*Thermus flavus*) DNA polymerase in 2× Reaction Buffer in a PCR with an annealing temperature of 55° C.

EXAMPLE XX

Selection of a Hotstart for Tth (*Thermus thermophilus*) DNA Polymerase from Poly-A Oligos with 100% Phosphorothioate Linkages S-oligos using poly-A sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGTTGACT-TAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tth (*Thermus thermophilus*) DNA polymerase, and either 5 µl water or 5 µl 20 aM DNA sequence: 5'GTTCCCCATTGTGGCAAA-GAAGGATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Tth (*Thermus thermophilus*) DNA polymerase in 2× Reaction Buffer in a PCR with an annealing temperature of 55° C.

EXAMPLE XXI

Selection of a Hotstart for Tli (*Thermococcus litoralis*) DNA Polymerase from Poly-A Oligos with 100% Phosphorothioate Linkages S-oligos using poly-A sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGTTGACT-TAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Tli (*Thermococcus litoralis*) DNA polymerase, and either 5 µl water or 5 µl 20 aM DNA sequence: 5'GTTCCCCATTGTGGCAAA-GAAGGATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Tli (*Thermococcus litoralis*) DNA polymerase in 2× Reaction Buffer in a PCR with an annealing temperature of 55° C.

EXAMPLE XXII

Selection of a Hotstart for Pfu (*Pyrococcus furiosus*) DNA Polymerase from Poly-AT Oligos with 100% Phosphorothioate Linkages S-oligos using poly-AT sequences (10-30 bases) with 100% phosphorothioate linkages are suspended at a 100 nM final concentration in 2× Reaction Buffer, a 500 nM primer pair (Forward sequence: GCGGTGAGGGGAATGTCTA (SEQ ID NO:5) and Reverse sequence: CAGCAAACGT-TGACTTAAAATCAGGA; SEQ ID NO:6), a 400 nM probe [6FAM] AGAGGCAACCCTGCACTGTTATGGGGC-CTACCTGGTTGCC [DABC] (SEQ ID NO:7), Pfu (*Pyrococcus furiosus*) DNA polymerase, and either 5 µl water or 5 µl 20 aM DNA sequence: 5'GTTCCCCATTGTGGCAAA-GAAGGATTTCAAGTACCGCGGTGAGGGGAATGTCT ATCACGAAGGGTTCTGCAAAGACGATA-GAGGCAACCCTGCACTGTTATGGGGCCT ACCTGAC-CATTGGGAAGAATCCTGATTTTAAGT-CAACGTTTGCTGTTTTGTGGGA GTCTAAGGGAGATAAGCCGGTGTAT-GAGCCGGGGTTT3' (SEQ ID NO:17) with a 10 µL final volume. Runs are performed in replicates of two. PCR conditions are 20 s at 95° C. followed by 45 cycles of 1s at 95° C., 20 s at 55° C. The largest s-oligo that does not delay the cycle threshold by more than 2 cycles, has the highest fluorescence, and has the best slope is selected as the non-limiting, but preferred, hotstart candidate for Pfu (*Pyrococcus furiosus*) DNA polymerase in 2× Reaction Buffer in a PCR with an annealing temperature of 55° C.

EXAMPLE XXIII

Selection of a Hotstart for GoScript™ Reverse Transcriptase from Poly-A Oligos with 100% Phosphorothioate Linkages S-oligos using poly-A sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAG-GAGA (SEQ ID NO:32) and Reverse sequence: CTGTGC-CTGGAGAGACAGCAGGA; SEQ ID NO:2), a 400 nM probe [6FAM] ACAGCATATTGACGCTGGGAAAGAC-CAGAGCGTCA [DABC] (SEQ ID NO:*), 5 u/µl GoTaq® DNA polymerase, GoScript™ Reverse Transcriptase, and either 5 µl water or 5 µl 200 fM RNA sequence: 5'

GGAAGCTGTACGCGTGGCATATTGGAC-TAGCGGTTAGAGGAGACCCCTCCCAC CACTGA-CAAAACGCAGCAAAAGGGGGCCCGAAGC-CAGGAGGAAGCTGTACTCCT GGTGGAAGGACTAGAGGTTAGAGGAGAC-CCCCCCAACACAAAAACAGCATATTG ACGCTGG-GAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for GoScript™ Reverse Transcriptase in GoTaq® buffer in a PCR with an annealing temperature of 55° C.

EXAMPLE XXIV

Selection of a Hotstart for GoScript™ Reverse Transcriptase from Poly-AT Oligos with 100% Phosphorothioate Linkages S-oligos using poly-AT sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAG-GAGA (SEQ ID NO:32) and Reverse sequence: CTGTGC-CTGGAGAGACAGCAGGA; SEQ ID NO:2), a 400 nM probe [6FAM] ACAGCATATTGACGCTGGGAAAGAC-CAGAGCGTCA [DABC] (SEQ ID NO:*), 5u/µl GoTaq® DNA polymerase, GoScript™ Reverse Transcriptase, and either 5 µl water or 5 µl 200 fM RNA sequence: 5' GGAAGCTGTACGCGTGGCATATTGGAC-TAGCGGTTAGAGGAGACCCCTCCCAC CACTGA-CAAAACGCAGCAAAAGGGGGCCCGAAGC-CAGGAGGAAGCTGTACTCCT GGTGGAAGGACTAGAGGTTAGAGGAGAC-CCCCCCAACACAAAAACAGCATATTG ACGCTGG-GAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for GoScript™ Reverse Transcriptase in GoTaq® buffer in a PCR with an annealing temperature of 55° C.

EXAMPLE XXV

Selection of a Hotstart for GoScript™ Reverse Transcriptase from Poly-ACTG Oligos with 100% Phosphorothioate Linkages S-oligos using poly-ACTG sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAG-GAGA (SEQ ID NO:32) and Reverse sequence: CTGTGC-CTGGAGAGACAGCAGGA (SEQ ID NO:2), a 400 nM probe [6FAM] ACAGCATATTGACGCTGGGAAAGAC-CAGAGCGTCA [DABC] (SEQ ID NO:*), 5 u/µl GoTaq® DNA polymerase, GoScript™ Reverse Transcriptase, and either 5 µl water or 5 µl 200 fM RNA sequence: 5' TTAGAG-GAGACCCCTCCCACCACTGACAAAACG-CAGCAAAAGGGGGCCCGAAG CCAGGAGGAAGCT-GTACTCCTGGTGGAAGGACTAGAGGTTAGAG GAGACCCCCC CAACACAAAAACAGCATAT-TGACGCTGGGAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for GoScript™ Reverse Transcriptase in GoTaq® buffer in a PCR with an annealing temperature of 55° C.

EXAMPLE XXVI

Selection of a Hotstart for AMV Reverse Transcriptase from Poly-A Oligos with 100% Phosphorothioate Linkages S-oligos using poly-A sequences (17, 19, 21, 23, and 25 bases) with 100% phosphorothioate linkages are Chloride, a 500 nM primer pair (Forward sequence: GGAAGCTG-TACGCGACTAGTGGTTAGAGGAGA (SEQ ID NO:32) and Reverse sequence: CTGTGCCTGGAGAGACAG-CAGGA; SEQ ID NO:2), a 400 nM probe [6FAM] ACAG-CATATTGACGCTGGGAAAGACCAGAGCGTCA [DABC] (SEQ ID NO:*), 5 u/µl GoTaq® DNA polymerase, AMV Reverse Transcriptase, and either 5 µl water or 5 µl 200 fM RNA sequence: 5' GGAAGCTGTACGCGTGGCATAT-TGGACTAGCGGTTAGAGGAGACCCCTCCCAC CACT-GACAAAACGCAGCAAAAGGGGGC-CCGAAGCCAGGAGGAAGCTGTACTCCT GGTGGAAGGACTAGAGGTTAGAGGAGAC-CCCCCCAACACAAAAACAGCATATTG ACGCTGG-GAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for AMV Reverse Transcriptase in GoTaq® buffer in a PCR with an annealing temperature of 55° C.

EXAMPLE XXVII

Selection of a Hotstart for AMV Reverse Transcriptase from Poly-AT Oligos with 100% Phosphorothioate Linkages S-oligos using poly-AT sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAG-GAGA (SEQ ID NO:32) and Reverse sequence: CTGTGC-CTGGAGAGACAGCAGGA; SEQ ID NO:2), a 400 nM probe [6FAM] ACAGCATATTGACGCTGGGAAAGAC-CAGAGCGTCA [DABC] (SEQ ID NO:*), 5 u/µl GoTaq® DNA polymerase, AMV Reverse Transcriptase, and either 5 µl water or 5 µl 200 fM RNA sequence: 5' GGAAGCTG-TACGCGTGGCATATTGGACTAGCGGTTA-GAGGAGACCCCTCCCAC CACTGACAAAACGCAG-CAAAAGGGGGCCCGAAGCCAGGAGGAAGCTG TACTCCT GGTGGAAGGACTAGAGGTTAGAG-GAGACCCCCCCAACACAAAAACAGCATATTG ACGCTGGGAAAGACCAGA 3' (SEQ ID NO:34) with a 10 µL final volume. Runs are performed in replicates of two.

PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for AMV Reverse Transcriptase in GoTaq® buffer in a PCR with an annealing temperature of 55° C.

EXAMPLE XXVIII

Selection of a Hotstart for AMV Reverse Transcriptase from Poly-ACTG Oligos with 100% Phosphorothioate Linkages S-oligos using poly-ACTG sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAGGAGA (SEQ ID NO:32) and Reverse sequence: CTGTGCCTGGAGAGACAGCAGGA; SEQ ID NO:2), a 400 nM probe [6FAM] ACAGCATATTGACGCTGGGAAAGACCAGAGCGTCA [DABC] (SEQ ID NO:*), 5 u/µl GoTaq® DNA polymerase, AMV Reverse Transcriptase, and either 5 µl water or 5 µl 200 fM RNA sequence: 5' GGAAGCTGTACGCGTGGCATATTGGACTAGCGGTTA-GAGGAGACCCCTCCCAC CACTGACAAAACGCAG-CAAAAGGGGGCCCGAAGCCAGGAGGAAG CTGTACTCCT GGTGGAAGGACTAGAGGTTAGAG-GAGACCCCCCAACACAAAAACAGCATATTG ACGCTGGGAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for AMV Reverse Transcriptase in GoTaq® buffer in a PCR with an annealing temperature of 55° C.

EXAMPLE XXIX

Selection of a Hotstart for M-MLV Reverse Transcriptase from Poly with 100% Phosphorothioate Linkages S-oligos using poly-A sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAGGAGA (SEQ ID NO:32) and Reverse sequence: CTGTGCCTGGAGAGACAGCAGGA; SEQ ID NO:2), a 400 nM probe [6FAM] ACAGCATATTGACGCTGGGAAAGACCAGAGCGTCA [DABC] (SEQ ID NO:*), 5 u/µl GoTaq® DNA polymerase, M-MLV Reverse Transcriptase, and either 5 µl water or 5 µl 200 fM RNA sequence: 5' GGAAGCTGTACGCGTGGCATATTGGACTAGCGGTTA-GAGGAGACCCCTCCCAC CACTGACAAAACGCAG-CAAAAGGGGGCCCGAAGCCAGGAGGAAGCTGT ACTCCT GGTGGAAGGACTAGAGGTTAGAGGAGAC-CCCCCCAACACAAAAACAGCATATTG ACGCTGG-GAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for M-MLV Reverse Transcriptase in GoTaq® buffer in a PCR with an annealing temperature of 55° C.

EXAMPLE XXX

Selection of a Hotstart for M-MLV Reverse Transcriptase from Poly-AT Oligos with 100% Phosphorothioate Linkages S-oligos using poly-AT sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAGGAGA (SEQ ID NO:32) and Reverse sequence: CTGTGCCTGGAGAGACAGCAGGA; SEQ ID NO:2), a 400 nM probe [6FAM] ACAGCATATTGACGCTGGGAAAGACCAGAGCGTCA [DABC] (SEQ ID NO:*), 5 u/µl GoTaq® DNA polymerase, M-MLV Reverse Transcriptase, and either 5 µl water or 5 µl 200 fM RNA sequence: 5' GGAAGCTGTACGCGTGGCATATTGGACTAGCGGTTA-GAGGAGACCCCTCCCAC CACTGACAAAACGCAG-CAAAAGGGGGCCCGAAGCCAGGAGGAAG CTGTACTCCT GGTGGAAGGACTAGAGGTTAGAG-GAGACCCCCCAACACAAAAACAGCATATTG ACGCTGGGAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for M-MLV Reverse Transcriptase in GoTaq® buffer in a PCR with an annealing temperature of 55° C.

EXAMPLE XXXI

Selection of a Hotstart for M-MLV Reverse Transcriptase from Poly-ACTG Oligos with 100% Phosphorothioate Linkages S-oligos using poly-ACTG sequences (10-30 bases) with 100% phosphorothioate linkages are suspended at a 100 nM final concentration in 2× GoTaq® Colorless master mix, 1 mM Magnesium Chloride, a 500 nM primer pair (Forward sequence: GGAAGCTGTACGCGACTAGTGGTTAGAGGAGA (SEQ ID NO:32) and Reverse sequence: CTGTGCCTGGAGAGACAGCAGGA; SEQ ID NO:2), a 400 nM probe [6FAM] ACAGCATATTGACGCTGGGAAAGACCAGAGCGTCA [DABC] (SEQ ID NO:*), 5 u/µl GoTaq® DNA polymerase, M-MLV Reverse Transcriptase, and either 5 µl water or 5 µl 200 fM RNA sequence: 5' GGAAGCTGTACGCGTGGCATATTGGACTAGCGGTTA-GAGGAGACCCCTCCCAC CACTGACAAAACGCAG-CAAAAGGGGGCCCGAAGCCAGGAGGAAGC TGTACTCCT GGTGGAAGGACTAGAGGTTAGAG-GAGACCCCCCAACACAAAAACAGCATATTG ACGCTGGGAAAGACCAGA 3' (SEQ ID NO:34) with a 10 µL final volume. Runs are performed in replicates of two. PCR conditions are 10 minutes at 55° C., 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for M-MLV Reverse Transcriptase in GoTaq® buffer in a PCR with an annealing temperature of 55° C.

EXAMPLE XXXII

Selection of a Hotstart for DNA Taq Polymerase from Poly-A Oligos with 100% Phosphorothioate Linkages (HBV)

S-oligos using poly-A sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGACCACTGGACAGGCATACTGGAAGCCATC ATCATCATGGGACCTAATTTCCCTTAAGCGAG-GAAACACTCCTAAGGATCAGGGC CCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXIII

Selection of a Hotstart for DNA Taq Polymerase from Poly-C Oligos with 100% Phosphorothioate Linkages (HBV)

S-oligos using poly-C sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGACCACTGGACAGGCATACTGGAAGCCATCA TCAT-CATGGGACCTAATTTCCCTTAAGCGAG-GAAACACTCCTAAGGATCAGGGCC CCTGTTATGATTCCTCGGTCTCCAGTG-GCGTCCAGGGTGCCACACCGGGGGGTCG ATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXIV

Selection of a Hotstart for DNA Taq Polymerase from Poly-G Oligos with 100% Phosphorothioate Linkages (HBV)

S-oligos using poly-G sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGACCACTGGACAGGCATACTGGAAGCCATC ATCAT-CATGGGACCTAATTTCCCTTAAGCGAG-GAAACACTCCTAAGGATCAGGGC CCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXV

Selection of a Hotstart for DNA Taq Polymerase from Poly-T Oligos with 100% Phosphorothioate Linkages (HBV)

S-oligos using poly-T sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37), and either 5 µl water or 5 µl 20 aM DNA sequence: 5' TACTGTGGCAAATGGGGATGTGAGACCACTGGACAGGCATACTGGAAGCCATC ATCAT-CATGGGACCTAATTTCCCTTAAGCGAG-GAAACACTCCTAAGGATCAGGGC CCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXVI

Selection of a Hotstart for DNA Taq Polymerase from Poly-AT Oligos with 100% Phosphorothioate Linkages (HBV)

S-oligos using poly-AT sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAG-GCATAAATTGGT (SEQ ID NO:35) and Reverse sequence: ACAGCTTGGAGGCTTGAACA; SEQ ID NO:36), a 400 nM probe [6FAM] CACCAGCACCATG-CAACTTTTTCACCTCTGCCTACATGGTGC [DABC] (SEQ ID NO:37), and either 5 µl water or 5 µl 20 aM DNA sequence: 5' TACTGTGGCAAATGGGGATGTGAGAC-CACTGGACAGGCATACTGGAAGCCATC ATCAT-CATGGGACCTAATTTCCCTTAAGCGAG-GAAACACTCCTAAGGATCAGGGC CCCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXVII

Selection of a Hotstart for DNA Taq Polymerase from Poly-ACTG Oligos with 100% Phosphorothioate Linkages (HBV)

S-oligos using poly-ACTG sequences (10-30 bases) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAG-GCATAAATTGGT (SEQ ID NO:35) and Reverse sequence: ACAGCTTGGAGGCTTGAACA; SEQ ID NO:36), a 400 nM probe [6FAM] CACCAGCACCATG-CAACTTTTTCACCTCTGCCTACATGGTGC [DABC] (SEQ ID NO:37), and either 5 µl water or 5 µl 20 aM DNA sequence: 5' TACTGTGGCAAATGGGGATGTGAGAC-CACTGGACAGGCATACTGGAAGCCATC ATCAT-CATGGGACCTAATTTCCCTTAAGCGAG-GAAACACTCCTAAGGATCAGGGC CCCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXVIII

Selection of a Hotstart for DNA Taq Polymerase from 30mer Poly-A Oligos with 10 to 30 Phosphorothioate Linkages (33-100%)

S-oligos using 30mer poly-A sequences with 10 to 30 phosphorothioate linkages (33-100%) are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAG-GCATAAATTGGT (SEQ ID NO:35) and Reverse sequence: ACAGCTTGGAGGCTTGAACA; SEQ ID NO:36), a 400 nM probe [6FAM] CACCAGCACCATG-CAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGAC-CACTGGACAGGCATACTGGAAGCCATC ATCAT-CATGGGACCTAATTTCCCTTAAGCGAG-GAAACACTCCTAAGGATCAGGGC CCCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XXXIX

Selection of a Hotstart for DNA Taq Polymerase from 20mer to 60mer Poly-A Oligos with 10 to 30 Phosphorothioate Linkages (50%)

S-oligos using 20mer to 60mer poly-A sequences with 10 to 30 phosphorothioate linkages (50%) are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAG-GCATAAATTGGT (SEQ ID NO:35) and Reverse sequence: ACAGCTTGGAGGCTTGAACA; SEQ ID NO:36), a 400 nM probe [6FAM] CACCAGCACCATG-CAACTTTTTCACCTCTGCCTACATGGTGC [DABC] (SEQ ID NO;37), and either 5 µl water or 5 µl 20 aM DNA sequence: 5' TACTGTGGCAAATGGGGATGTGAGAC-CACTGGACAGGCATACTGGAAGCCATC ATCAT-CATGGGACCTAATTTCCCTTAAGCGAG-GAAACACTCCTAAGGATCAGGGC CCCTGTTATGATTCCTCGGTCTCCAGTG-GCGTCCAGGGTGCCACACCGGGGGGTC GATG-CAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XL

Selection of a Hotstart for DNA Taq Polymerase from a Randomer Sequence with 100% Phosphorothioate Linkages S-oligos from 10 to 30 bases taken from the 5' segment of a 30 base randomer (TGCATAGGCT CGCGATTCAA TGTGAGCAGA) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGACCACTGGACAGGCATACTGGAAGCCATC ATCATCATGGGACCTAATTTCCCTTAAGCGAGGAAACACTCCTAAGGATCAGGGC CCCTGTTATGATTCCTCGGTCTCCAGTGGCGTCCAGGGTGCCACACCGGGGGTC GATGCAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XLI

Selection of a Hotstart for DNA Taq Polymerase from a Second Randomer Sequence with 100% Phosphorothioate Linkages S-oligos from 10 to 30 bases taken from the 5' segment of a 30 base randomer (CCGATACGCGATGCGACTGT GCAGCATGCA; SEQ ID NO:38) with 100% phosphorothioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGCAAATGGGGATGTGAGACCACTGGACAGGCATACTGGAAGCCATC ATCATCATGGGACCTAATTTCCCTTAAGCGAGGAAACACTCCTA AGGATCAGGGC CCCTGTTATGATTCCTCGGTCTCCAGTGGCGTCCAGGGTGCCACACCGGGGGTC GATGCAACCCCCTGGTCTTAGAATTC 3' (SEQ ID NO:12) with a 10 µL final volume. Runs are performed in replicates of two. PCR conditions were 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the non-limiting, but preferred, hotstart candidate for Taq polymerase in Simplex DNA Master Mix in a PCR with an annealing temperature of 55° C.

EXAMPLE XLII

Selection of a Hotstart for DNA Taq Polymerase from Poly-A Oligos with 100% Phosphorodithioate Linkages S-oligos using poly-A sequences (5-30 bases) with 100% phosphorodithioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37, and either 5 µl water or 5 µl 20 aM DNA sequence: 5' TACTGTGGCAAATGGGGATGTGAGACCACTGGACAGGCATACTGGAAGCCATC ATCATCATGGGACCTAATTTCCCTTAAGCGAGGAAACACTCCTAAGGATCAGGGC CCCTGTTATGATTCCTCGGTCTCCAGTGGCGTCCAGGGTGCCACACCGGGGGTC GATGCAACCCCCTGGTCTTAGAATTC 3' (SEQ ID NO:12) with a 10 µL final volume. Runs are performed in replicates of two. PCR conditions are 20 s at 95° C. followed by 45 cycles of 1 s at 95° C., 20 s at 55° C. The largest s-oligo that does not delay the cycle threshold by more than 2 cycles, has the highest fluorescence, and has the best slope is selected as the preferred, but non-limiting, hotstart candidate for Taq polymerase in Simplex DNA Master Mix in a PCR with an annealing temperature of 55° C.

EXAMPLE XLIII

Selection of a Hotstart for DNA Taq Polymerase from poly-A Oligos with 100% Phosphorodithioate Linkages Using Agarose Gel Electrophoresis S-oligos using poly-A sequences (5-30 bases) with 100% phosphorodithioate linkages are suspended at a 100 nM final concentration in Simplex DNA Master Mix [Cat. # S1001, Cooperative Diagnostics, Greenwood, S.C.], a 500 nM primer pair (Forward sequence: AGGAGGCTGTAGGCATAAATTGGT (SEQ ID NO:35) and Reverse sequence: ACAGCTTGGAGGCTTGAACA; SEQ ID NO:36), a 400 nM probe [6FAM] CACCAGCACCATGCAACTTTTTCACCTCTGCCTACATGGTGC [DABC] (SEQ ID NO:37), and either 5 µl water or 5 µl 20 aM DNA sequence: 5' TACTGTGGCAAATGGGGATGTGAGACCACTGGACAGGCATACTGGAAGCCATC ATCATCATGGGACCTAATTTCCCTTAAGCGAGGAAACACTCCTAAGGATCAGGGC CCCTGTTATGATTCCTCGGTCTCCAGTGGCGTCCAGGGTGCCACACCGGGGGTC GATGCAACCCCCTGGTCTTAGAATTC 3' (SEQ ID NO:12) with a 10 µL final volume. Runs are performed in replicates of two. PCR conditions are 20 s at 95° C. followed by 45 cycles of 1 s at 95° C., 20 s at 55° C. The s-oligo that has the greatest size product band and least primer dimer band is selected as the preferred, but non-limiting, hotstart candidate for Taq polymerase in Simplex DNA Master Mix in a PCR with an annealing temperature of 55° C.

What is claimed is:

1. A method of preventing non-specific reaction of a nucleotide sequence with a DNA modifying enzyme, comprising:
designing an oligonucleotide that comprises from about 5 to about 50 nucleotides, wherein about 40% to 100% of the nucleotides comprise a sulfur atom and wherein the oligonucleotide is not a primer, and has a 3' cap to prevent extension by a polymerase; and
contacting the oligonucleotide with at least one nucleic acid modifying enzyme, wherein the nucleic acid modifying enzyme is a polymerase; and
performing amplification in the presence of the oligonucleotide, a primer, and the polymerase, wherein the oligonucleotide reduces enzymatic activity of the polymerase at or below room temperature, but that reduces enzymatic activity to a lesser degree at the reaction temperature, which is above room temperature;
and wherein the oligonucleotide reduces nonspecific products produced by the polymerase;
further wherein said oligonucleotide is comprised of polyA bases.

2. The method of claim 1, wherein said sulfur atom is part of a phosphorothioate linkage.

3. The method of claim 2, wherein said phosphorothioate linkage comprises at least 50%, at least 70%, or at least 90% of the oligonucleotide.

4. The method of claim 1, wherein the nucleic acid amplification is reverse transcriptase PCR and the polymerase is reverse transcriptase.

5. The method of claim 1, wherein the polymerase is DNA polymerase.

* * * * *